US008590531B2

(12) United States Patent
Rouse et al.

(10) Patent No.: US 8,590,531 B2
(45) Date of Patent: Nov. 26, 2013

(54) MANIFOLD FOR USE IN MEDICAMENT DISPENSER

(75) Inventors: Colin John Rouse, Hertfordshire (GB); Richard Ian Walker, Hertfordshire (GB)

(73) Assignee: Glaxo Group Limited, Brentford, Middlesex (GB)

( * ) Notice: Subject to any disclaimer, the term of this patent is extended or adjusted under 35 U.S.C. 154(b) by 1042 days.

(21) Appl. No.: 11/722,185

(22) PCT Filed: Dec. 19, 2005

(86) PCT No.: PCT/EP2005/013840

§ 371 (c)(1), (2), (4) Date: Oct. 26, 2009

(87) PCT Pub. No.: WO2006/066910

PCT Pub. Date: Jun. 29, 2006

(65) Prior Publication Data

US 2010/0037894 A1 Feb. 18, 2010

(30) Foreign Application Priority Data

Dec. 20, 2004 (GB) .................................. 0427858.6

(51) Int. Cl.

| | |
|---|---|
| ***A61M 15/00*** | (2006.01) |
| ***A61M 16/00*** | (2006.01) |
| ***B05D 7/14*** | (2006.01) |
| ***B65D 83/06*** | (2006.01) |

(52) U.S. Cl.
USPC ................................ 128/203.19; 128/203.15

(58) Field of Classification Search
USPC ............. 128/200.14, 200.18, 200.21–200.23, 128/203.12, 203.15, 203.19, 203.21, 203.23
See application file for complete search history.

(56) References Cited

U.S. PATENT DOCUMENTS

| | | | |
|---|---|---|---|
| 2,587,215 | A | 2/1952 | Priestly |
| 3,565,071 | A | 2/1971 | Cobb et al. |

(Continued)

FOREIGN PATENT DOCUMENTS

| | | | |
|---|---|---|---|
| CA | 2093809 | A1 | 2/1993 |
| CN | 2614064 | Y | 5/2004 |

(Continued)

OTHER PUBLICATIONS

Co-Pending U.S. Appl. No. 11/722,193, filed Jun. 20, 2007.

(Continued)

*Primary Examiner* — Kristen Matter
(74) *Attorney, Agent, or Firm* — James P. Riek

(57) ABSTRACT

A manifold for a medicament dispenser, where a manifold body defines a chimney with an inlet and an exit for directing airflow from the inlet to the exit, and a chamber with a chamber inlet and chamber exit. The chimney exit and the chamber inlet lie side-by-side each other such that when the open blister pocket of the blister pack is positioned adjacent thereto, the airflow may be directed from the chimney exit to the chamber inlet via the open blister pocket to entrain the medicament powder, enabling transport of powder in the airflow from chamber inlet to chamber outlet. The chimney creates turbulence in the airflow at the open blister pocket. The manifold comprises plural chimney exits, located at an angle relative to each other of from 150° to 30° such that, in use, plural airflow jets are directed at different and conflicting angles towards the open blister pocket.

3 Claims, 18 Drawing Sheets

(56) References Cited

U.S. PATENT DOCUMENTS

| | | | | |
|---|---|---|---|---|
| 3,973,566 | A | 8/1976 | Mathes | |
| 5,035,237 | A | 7/1991 | Newell et al. | |
| 5,239,993 | A | 8/1993 | Evans | |
| 5,372,128 | A | 12/1994 | Haber et al. | |
| 5,469,843 | A | 11/1995 | Hodson | |
| 5,492,112 | A | 2/1996 | Mecikalski et al. | |
| 5,533,502 | A | 7/1996 | Piper | |
| 5,590,645 | A | 1/1997 | Davies et al. | |
| 5,619,985 | A | 4/1997 | Ohki et al. | |
| 5,657,749 | A | 8/1997 | Cox | |
| 5,685,294 | A | 11/1997 | Gupte et al. | |
| 5,694,920 | A | 12/1997 | Abrams et al. | |
| 5,715,810 | A | 2/1998 | Armstrong et al. | |
| 5,740,794 | A | 4/1998 | Smith et al. | |
| 5,765,552 | A | 6/1998 | Zanen et al. | |
| 5,881,719 | A | 3/1999 | Gottenauer et al. | |
| 6,029,661 | A | 2/2000 | Whaley et al. | |
| 6,065,472 | A | 5/2000 | Anderson et al. | |
| 6,209,538 | B1 | 4/2001 | Casper et al. | |
| 6,273,086 | B1 | 8/2001 | Ohki et al. | |
| 6,615,826 | B1 | 9/2003 | Gabrio et al. | |
| 6,655,381 | B2 | 12/2003 | Keane et al. | |
| 6,715,485 | B1 | 4/2004 | Djupesland | |
| 6,722,364 | B2 | 4/2004 | Connelly et al. | |
| 6,792,945 | B2 | 9/2004 | Davies et al. | |
| 6,845,772 | B2 | 1/2005 | Braithwaite et al. | |
| 6,983,748 | B2 | 1/2006 | Brown et al. | |
| 2001/0029948 | A1 * | 10/2001 | Ingle et al. | 128/203.15 |
| 2002/0053344 | A1 | 5/2002 | Davies et al. | |
| 2003/0183229 | A1 | 10/2003 | Smith et al. | |
| 2004/0025875 | A1 | 2/2004 | Reber et al. | |
| 2004/0168687 | A1 | 9/2004 | Asking et al. | |
| 2004/0250812 | A1 | 12/2004 | Davies et al. | |
| 2005/0268909 | A1 | 12/2005 | Bonney et al. | |
| 2006/0196504 | A1 | 9/2006 | Augustyn et al. | |
| 2007/0137645 | A1 | 6/2007 | Eason et al. | |

FOREIGN PATENT DOCUMENTS

| | | | |
|---|---|---|---|
| EP | 0711572 | | 5/1996 |
| EP | 0745401 | | 12/1996 |
| EP | 1062962 | | 12/2000 |
| JP | 9-140794 | | 3/1997 |
| JP | 9140794 | A | 6/1997 |
| WO | 9209322 | A1 | 6/1992 |
| WO | WO 94/06497 | | 3/1994 |
| WO | 9408552 | A2 | 4/1994 |
| WO | 9725086 | A2 | 7/1997 |
| WO | 9740876 | A2 | 11/1997 |
| WO | WO 99/13930 | | 3/1999 |
| WO | WO 99/47099 | | 9/1999 |
| WO | 0064520 | A1 | 11/2000 |
| WO | WO 01/26720 | | 4/2001 |
| WO | 0200280 | A2 | 1/2002 |
| WO | 0224263 | A2 | 3/2002 |
| WO | 02053216 | A2 | 7/2002 |
| WO | 02089881 | A1 | 11/2002 |
| WO | 03061743 | A1 | 7/2003 |
| WO | 03075988 | A1 | 9/2003 |
| WO | 2004011067 | A1 | 2/2004 |
| WO | WO 2004/093848 | * | 11/2004 |
| WO | 2005002654 | A2 | 1/2005 |
| WO | 2005014089 | A1 | 2/2005 |
| WO | 2005037353 | A1 | 4/2005 |
| WO | 2006066908 | A1 | 6/2006 |
| WO | 2006066909 | A1 | 6/2006 |
| WO | 2007012871 | A1 | 2/2007 |

OTHER PUBLICATIONS

Co-Pending U.S. Appl. No. 11/722,188, filed Jun. 20, 2007.

Co-pending U.S. Appl. No. 12/096,820, filed Jun. 10, 2008.

Co-pending U.S. Appl. No. 12/096;823, filed Jun. 10, 2008.

Office Action dated Jul. 21, 2011 for U.S. Appl. No. 12/096,820.

Amendment and Terminal Disclaimer filed Oct. 18, 2011 in response to Office Action dated Jul. 21, 2011 for U.S. Appl. No. 12/096,820.

Notice of Allowance dated Dec. 2, 2011 for U.S. Appl. No. 12/096,820.

Simons; "Chapter 51: Antihistamines"; Middleton's Allergy: Principles and Practice, 6th Ed.; 2003; pp. 834-869.

Office Action dated Oct. 19, 2010 for U.S. Appl. No. 11/722,188.

Amendment filed Jan. 18, 2011 in response to Office Action dated Oct. 19, 2010 for U.S. Appl. No. 11/722,188.

Final Office Action dated Feb. 8, 2011 for U.S. Appl. No. 11/722,188.

Amendment After Final filed Mar. 29, 2011 in response to Final Office Action dated Feb. 8, 2011 for U.S. Appl. No. 11/722,188.

Advisory Action dated Apr. 6, 2011 in response to 37 CFR 1.312 Amendment After Final dated Mar. 29, 2011 for U.S. Appl. No. 11/722,188.

Non-Final Office Action issued Nov. 10, 2011 for U.S. Appl. No. 12/096,823.

Amendment filed Feb. 8, 2012 in response to Non-Final Office Action issued Nov. 10, 2011 for U.S. Appl. No. 12/096,823.

Final Office Action issued Apr. 13, 2012 for U.S. Appl. No. 12/096,823.

RCE with Amendment filed Jul. 11, 2012 in response to Final Office Action issued Apr. 13, 2012 for U.S. Appl. No. 12/096,823.

Office Action dated May 7, 2013 for U.S. Appl. No. 12/096,823.

* cited by examiner

MANIFOLD FOR USE IN MEDICAMENT DISPENSER

CROSS-REFERENCE TO RELATED APPLICATIONS

This application is filed pursuant to 35 U.S.C. §371 as a United States National Phase Application of International Application No. PCT/EP2005/013840 filed 19 Dec. 2005, which claims priority from GB0427858.6 filed 20 Dec. 2004.

TECHNICAL FIELD

The present invention relates to a manifold for use in a medicament dispenser for dispensing dry powder medicament from a blister pack form medicament carrier. The manifold assists effective release of medicament powder from an opened blister pocket to a mouthpiece of the dispenser, and thence for inhalation by a patient.

BACKGROUND TO THE INVENTION

The use of inhalation devices in the administration of medicaments, for example in bronchodilation therapy is well known. Such devices generally comprise a body or housing within which a medicament carrier is located. Known inhalation devices include those in which the medicament carrier is a blister pack containing a number of blister pockets for containment of medicament in dry powder form. Such devices typically contain a mechanism for accessing a medicament dose by opening one or more blister pockets. The mechanism for example, comprises either piercing means or peeling means to peel a lid sheet away from a base sheet of the blister pack. The powdered medicament is then liberated from the opened blister pocket(s) for inhaled delivery to the patient.

Inhalation devices of the type described above comprise an element, generally referred to as a manifold, for guiding airflow towards one or more opened blister pocket(s) for liberating the powder contained therein; and subsequently guiding that liberated powder to a mouthpiece for inhalation by a patient. It is appreciated that the characteristics of the manifold are important in both ensuring effective liberation of powder and in subsequent guiding that liberated powder to the mouthpiece.

The Applicant has now appreciated that the form of the manifold can affect the particle size characteristics of the liberated medicament powder, which characteristics are known to be pharmaceutically important. In particular, the Applicant has appreciated that fine particle fraction can be influenced by the form of the manifold. As known in the art, "fine particle fraction" or FP Fraction generally refers to the percentage of particles within a given dose of aerosolized medicament that is of "respirable" size. It is desirable that the form of the manifold acts such as to increase the FP Fraction of the liberated powder that is made available at the mouthpiece for inhalation by the patient.

In one aspect, the Applicant has now found that the liberation of powder from the pocket is enhanced if a turbulent (e.g. high shear) airflow is directed towards the pocket. Such enhancement can be of particular value where liberation of the powder from the pocket is otherwise difficult to achieve in a conventional airflow.

SUMMARY OF THE INVENTION

According to one aspect of the invention there is provided a manifold for use in a medicament dispenser device for the delivery of medicament powder from an open blister pocket of a blister pack, the manifold comprising a body, said body defining a chimney having a chimney inlet and a chimney exit for directing an airflow from said chimney inlet to said chimney exit;

the body further defining a chamber having a chamber inlet and a chamber exit, wherein the chimney exit and said chamber inlet lie side-by-side each other such that when said open blister pocket of said blister pack is positioned adjacent thereto said airflow may be directed from the chimney exit to the chamber inlet via the open blister pocket to entrain said medicament powder and enable transport thereof in the airflow from the chamber inlet to said chamber outlet, and wherein the chimney is arranged to create turbulence in the airflow at the open blister pocket.

There is provided a manifold for use in a medicament dispenser device for the delivery of medicament powder from an open blister pocket of a blister pack.

The manifold comprises a body that is generally sized and shaped for receipt by a medicament dispenser device, of which it typically comprises a component part. The manifold itself may either be comprised as a single, integral component or as a sub-assembly or part of an adjacent component, and is typically formed as a moulded part.

In aspects, the manifold is either integral with or separable from the other components of the medicament dispenser device. In one aspect, the manifold is provided as a snap-fit component to the medicament dispenser device, and the manifold and/or medicament dispenser device is provided with snap-fit features to enable this mode of fitting.

Suitably, the manifold body is arranged for receipt by a medicament dispenser device at a location that is intermediate between a mouthpiece for the delivery of medicament in inhaled form by a patient; and an opening station, at which an opened blister pocket of the blister pack is presented to the manifold (i.e. at which its medicament contents may be accessed and entrained).

The body of the manifold defines a chimney that has a chimney inlet and a chimney exit. Air may be drawn through the chimney inlet (e.g. as a result of patient inhalation) to create airflow therein. The chimney directs that airflow from the chimney inlet to the chimney exit.

The body of the manifold also defines a chamber that has a chamber inlet and a chamber exit. Air and particles entrained therein (see below) may be drawn through the chamber inlet to the chamber exit. A mouthpiece generally locates adjacent to the chamber exit and in one aspect, that part of the body defining the chamber exit and the mouthpiece comprise a common component.

The chimney exit and chamber inlet lie side-by-side (i.e. adjacent or close to) each other such that when said open blister pocket of said blister pack is positioned adjacent thereto the airflow may be directed from the chimney exit to the chamber inlet via the open blister pocket to entrain the medicament powder contents thereof. Transport of the so-entrained medicament particles is thereby enabled in the airflow from the chamber inlet to the chamber outlet.

In aspects, the manifold geometry is arranged such that only a proportion of the airflow through the manifold is directed towards the open blister pocket. Suitably, from 3 to 50%, preferably from 5 to 15% of the airflow (e.g. about 10%) is directed towards the open blister pocket.

The manifold herein is suitable for use in a medicament dispenser device in which the patient breathes in to create the airflow through the manifold. The manifold and medicament dispenser device herein is designed to be suitable for use by a patient (e.g. asthmatic) with relatively poor breathing ability. A typical asthmatic patient might achieve a flow rate of around 30 to 100 liters/min through a medicament dispenser device.

Typically, the manifold provides an airflow resistance of 1 to 5 kPa (e.g. 2–3 kPa) for a typical airflow of 60 liters/minute, at which flow rate around 10% of the airflow is directed through the open pocket. The airflow may also vary, typically being from 30 to 100 liters/minute.

It will be appreciated that in use, the pressure drop and flow rate achievable by a patient depends upon both the level of airflow resistance of the manifold and/or medicament dispenser device and the breathing ability (respiratory effort) of the patient. As will be appreciated from the later description, bleed holes in particular, may be used to control the airflow resistance of the manifold.

The airflow resistivity of a particular manifold and/or medicament dispenser device can be found by dividing the square root of the pressure drop (in kPa) by the flow rate (in liters/min). Low airflow resistivity of the manifold and/or medicament dispenser device is generally preferable because it enables the patient to take a deep breath and thereby transport the medicament particles (as delivered from the dispenser device) to the lung.

It will be appreciated that the exact orientation of the chimney exit and chamber inlet will be determined to an extent by the shape of the blister pocket, and the desired function of entrainment of medicament particles in airflow. In one aspect, the open blister pocket has a generally elongate oval profile and the chimney exit and chamber inlet lie side-by-side and in use, are positioned above opposite ends of the elongate oval open pocket profile.

It will also be appreciated that the shape and dimensions of the chimney exit and chamber inlet will be determined to an extent by the shape of the blister pocket, and the desired function of entrainment of medicament particles in airflow. It has been found that reducing the cross-sectional area of chimney exit and chamber inlet can improve FP fraction performance at the expense of increased airflow resistance and potentially a reduction in pocket emptying performance. In one aspect, the chimney exit and chamber inlet define an essentially circular profile and have a diameter of from 2-7 mm, particularly 3-5 mm.

The chimney exit and chamber inlet may each comprise one or more simple openings (i.e. apertures) or alternatively, in aspects certain features may be provided thereto including a ‘cross-piece’ (e.g. cruciform-shaped) provided at the opening(s) of one or both thereof.

The chimney herein, is arranged to create turbulence in the airflow at the open blister pocket. That is to say, the chimney is arranged such that in use, turbulent airflow is presented at the open blister pocket. Such turbulent airflow has been found to assist in the entrainment of the medicament powder contents of the open blister pocket, and thereby to assist in emptying of the pocket of its medicament powder contents.

In one aspect, the turbulence arises as a result of the creation of shear stress, which assists in entrainment of the medicament powder by the airflow. Shear stress is generally defined to mean velocity gradient normal to the direction of airflow. Thus, a region of high shear stress (‘high shear’) is one in which there is a relatively large velocity gradient over a relatively short distance.

The Applicant has found that the presence of such turbulence can be particularly beneficial where the medicament powder comprises non-cohesive powder components (e.g. one that is non-sticky or only loosely associated e.g. non-agglomerated). The well-known Carr Index may be used to quantify the cohesiveness of a particular powder for delivery by the manifold and medicament dispenser device herein. Methods for measuring Carr Index are described in the following references: Carr, R L (1965) Chem Eng 72(1) page 162; Carr, R L (1965) Chem Eng 72(2) page 69; and Pharmaceutics: The Science of Dosage Form (1988) Ed. Aulton, M E, Churchill Livingstone, N.Y.

In one aspect herein, turbulent flow is created at the open blister pocket by providing plural chimney exits to the chimney, each of which directs airflow at the open blister pocket. In one particular aspect, the plural chimney exits are positioned such that in use, plural airflow jets are directed towards each other to produce a turbulent (e.g. high shear) interaction. The plural chimney exits (and hence, plural airflow jets) are suitably positioned at an angle (θ) relative to each other wherein θ is typically from 150° to 30°, preferably from 120° to 60°.

In another aspect herein, turbulent flow is created at the open blister pocket by shaping the chimney and/or chimney exits to produce a non-linear airflow. In one particular aspect, the chimney and/or chimney exits are shaped to produce a helical (e.g. vortex-like) airflow that is inherently turbulent.

In a further aspect herein, an obstacle is positioned within the chimney and/or at the chimney exit to disruptively create a non-linear airflow. In one particular aspect, a crosspiece or divider (e.g. knife-edge form) is provided within the chimney and/or at the chimney exit to disrupt the airflow and to produce turbulent regions of high shear stress.

The chimney herein, is arranged to create regions of acceleration or deceleration in the airflow at the open blister pocket. That is to say, the chimney is arranged such that in use, accelerating or decelerating airflow is presented at the open blister pocket. Such accelerating or decelerating airflow (whether turbulent or not) has been found to assist in the entrainment of the medicament powder contents of the open blister pocket, and thereby to assist in emptying of the pocket of its medicament powder contents.

The manifold herein provides that entrained medicament powder is transported via the chamber by airflow from the chamber inlet to the chamber outlet. The form and arrangement of that chamber has been found to potentially affect the overall performance (e.g. FP fraction performance) of the manifold.

In particular, the Applicant has found it to be beneficial that the chamber is arranged to promote break up (e.g. to de-aggregate or de-agglomerate) of the entrained powder that is transported there through. In particular, exposing the entrained powder to regions of differential force during its passage through the chamber has been found to assist in promoting the desired powder break up.

It has been found that the promotion of such break up can be particularly beneficial where the medicament powder comprises cohesive powder components (e.g. one that comprises particles that tend to associate with one another or one in which the particles are agglomerated).

In one aspect, it has been found that powder break up may be promoted in the chamber if the chamber is arranged such that regions of high differential force (e.g. high shear) that act on the entrained particles are created therein. That is to say, powder break up is promoted if the airflow/entrained powder experience one or more regions of high differential force on flowing through the chamber. Preferably, the overall geometry of the chamber is arranged such as to direct the airflow/entrained powder towards these regions of high differential force.

Suitable regions of high shear may be created if the diameter and/or shape varies along its length (i.e. along the path of airflow that it defines) such that airflow and entrained powder flowing therethrough tend to encounter walls of the chamber. Such encounters with walls are always regions of high shear (i.e. high speed or airflow next to low speed of airflow) because at the wall itself the airflow speed is effectively zero.

In another aspect, it has been found that powder break up may be promoted in the chamber if the chamber is arranged such that regions of accelerating or decelerating airflow are created therein. That is to say, powder break up is promoted if an airway and entrained powder experiences region of accelerating or decelerating airflow on flowing through the chamber. Preferably, the overall geometry of the chamber is arranged such as to direct the airflow carrying the entrained particles into these regions of accelerating airflow.

It will be appreciated that in use, the presence or otherwise of accelerating or decelerating airflow in the manifold herein can depend on either the patient inhalation profile or the manifold geometry. Thus, a patient inhalation profile that involves a change from slow inhalation to rapid inhalation will result in a 'patient created' region of accelerating airflow. On the other hand, a manifold geometry that (for any patient inhalation profile) results in regions of slow moving airflow being created adjacent to regions of fast moving airflow results a desired region of accelerating airflow. Alternatively, the manifold may be provided with features such as flaps or valves that open up in response to a particular airflow pressure thereby creating an 'acceleration' from zero flow (i.e. flap or valve closed) to permitted flow (i.e. flap or valve open).

Suitably, in use, the manifold is arranged to modify the effect of a user's inhalation profile to increase the acceleration experienced by the powder when it is aerosolised in the blister pocket.

Suitably, in use, the manifold is arranged to modify the effect of a user's inhalation profile to increase the acceleration experienced by the powder as it travels through the chamber from the blister pocket to the patient.

Enhanced propensity for a given patient inhalation profile to give rise to regions of accelerating airflow may be created if the cross-sectional area (e.g. diameter) of the chamber is reduced in the direction of flow. It will be appreciated that a smaller cross-sectional area will mean that the air has a higher velocity for a given flow rate. The acceleration for a given inhalation profile will therefore be proportionally greater.

Suitable regions of accelerating or decelerating airflow also may be created at the manifold if the cross-sectional area (e.g. diameter) of the chamber is arranged to vary in diameter, for example to narrow along its length (i.e. along the path of airflow that it defines) such that airflow and entrained powder flowing there through encounters a narrower cross-section or alternatively to broaden along its length (i.e. along the path of airflow that it defines) such that airflow and entrained powder flowing there through encounters a broader cross-section.

It will be appreciated that any such reduction of chamber cross-sectional area will also result in increased airflow resistance, and therefore may potentially impact the effectiveness of emptying of the opened blister pocket of its medicament contents. A compromise between creating regions of accelerating airflow by reducing chamber cross-sectional area (good for powder break up) and increasing airflow resistance (and potentially impacting upon pocket emptying) must therefore be struck.

In one aspect, the diameter of a chamber of circular profile narrows from about 14-16 mm at the chamber inlet end to about 5-8 mm at the chamber exit end.

In another aspect, the diameter of a chamber of circular profile is about 5-7 mm across its entire length (as opposed to a conventional diameter of about 14-16 mm).

In a further aspect, it has been found that powder break up may be promoted in the chamber if the chamber is arranged such that mechanical obstacles are created therein. That is to say, powder break up is promoted if an airflow/entrained powder experiences mechanical obstacles on flowing through the chamber.

Suitable mechanical obstacles that may be provided to the chamber comprise or consist of baffles, propellers, paddles, vanes and venturi forms. Alternatively, the chamber itself may be shaped with features (e.g. with defined surface indentations or protrusions) that provide mechanical obstacles.

In a still further aspect, it has been found that powder break up may be promoted in the chamber if the chamber is provided with one or more bleed holes thereto that direct bleed airflow jets in such a way as to disruptively impact the airflow that carries the entrained particles. That is to say, powder break up is promoted if one or more bleed holes directed in a particular way are provided to the chamber. The purpose of the bleed holes is to enable bleed air to be drawn into the chamber, which bleed air is directed to create regions of high shear and/or accelerating air that disruptively interacts with the airflow in which the powder is entrained.

The bleed holes typically have a cross-sectional area of from 1-20 $mm^2$, preferably from 2-8 $mm^2$. The bleed holes may define any suitable profile including oval and circular. In one aspect, the bleed holes are circular and have a diameter of from 1-5 mm, preferably from 1.5-3 mm.

In one aspect, the one or more bleed holes are arranged such as to direct bleed air jets at particular regions in the chamber thereby creating regions of high shear/turbulence therein.

Suitably, the one or more of the bleed holes are directed towards a wall of the chamber, thereby creating a region of high shear close to that wall and causing the particles to collide with said wall. Preferably, the overall geometry of the chamber is arranged such as to direct the airflow into these regions of high shear and/or to cause collisions with the wall. An additional advantage of directing bleed air at walls of the manifold is to prevent deposition of medicament particles thereon.

Suitably, the one or more of the bleed holes are directed towards each other such that the resulting bleed jets interact with each other to create regions of high shear. Preferably, the overall geometry of the chamber is arranged such as to direct the airflow into these regions of high shear.

Suitably, in use, the one or more bleed holes direct one or more air jets to impact upon at least one internal surface of the chamber to create at least one zone of high shear thereat, greater than 3 Pa at an air flow rate of 60 liters/minute.

Suitably, in use, medicament powder from the pocket is directed into said at least one zone of high shear to break up any agglomerate particle components thereof.

Suitably, in use, the at least one zone of high shear acts such as to reduce the deposition of powder on said at least one internal surface of the chamber.

It will be appreciated that the provision of such one or more bleed holes also result in reduced airflow resistance because a proportion of the airflow is not being drawn across the open blister pocket. The provision of bleed holes may therefore potentially to impact the effectiveness of emptying of the opened blister pocket of its medicament contents. A compromise between the creation of regions of accelerating airflow by providing bleed holes (good for powder break up) and the reduction of airflow resistance (and potentially impacting upon pocket emptying) must therefore be struck. As a general rule, the airflow resistance of the manifold should not be reduced to below a level wherein pocket emptying is compromised at a minimum flow rate of 30 liters/min.

Typically, the manifold herein is arranged such that from 5 to 50% (e.g. 10%) of the airflow is directed towards the open blister pocket. The remainder of the airflow is therefore not directed towards the open blister pocket, and for example is drawn through the bleed holes. In general terms, for a weakly cohesive powder it is desirable that less airflow is directed through the pocket than for a strongly cohesive powder.

In aspects herein, the size and/or location of any inlet, outlet and/or bleed hole(s) of the manifold is tuned to achieve the desired level of airflow through the pocket and/or airflow resistance and/or shear within the manifold, in use. It will be appreciated that such tuning may take into account the cohesiveness or otherwise of the medicament powder to be delivered through the manifold.

The Applicant has also found that manifold performance herein is enhanced if the manifold is arranged such as to delay the emptying of the medicament powder contents of the blister pocket.

In one aspect such delay is achieved by reducing the amount of airflow through the open blister pocket. Such reduction must not however, be too pronounced since insufficient airflow through the pocket can prevent the complete emptying of the medicament contents of the open blister pocket. Such reduction of airflow through the open blister pocket may be achieved by providing the manifold with one or more bleed holes positioned such as to ‘divert’ airflow from the opened pocket.

The Applicant has in particular, found that manifold performance herein is enhanced manifold is arranged such as to delay the emptying of the medicament powder contents of the blister pocket until regions of differential force (e.g. high shear/accelerating air) capable of causing powder break up are created in the chamber. If the pocket empties too early the powder to be broken up will have passed the through the high differential force zones before they are fully established so delaying the emptying of the pocket will improve manifold performance by ensuring that more of the powder experiences a region of high shear.

Suitably, the manifold herein is arranged such as to delay the emptying of the medicament powder contents of the blister pocket until a predetermined flow rate through the manifold chamber (i.e. not just through the blister pocket) is achieved by the inhaling patient. Whilst the value for the predetermined flow rate may be fine tuned, it is generally desirable that it has a value of between 5 to 45 liters/minute, preferably 20 to 30 liters/minute.

Desirably, the manifold herein acts overall such as to enhance the uniformity of medicament dose delivered thereby.

Desirably, the manifold herein acts overall such as to increase the Emitted Dose (ED) of the medicament powder that is made available at the chamber exit/mouthpiece for inhalation by the patient. The ED is generally measured by collecting the total amount of medicament powder emitted from the dispenser device for example, using a dose sampling apparatus such as a Dose Uniformity Sampling Apparatus (DUSA). The ED may also be expressed as a percentage (% ED) of the measured dose (MD) contained within the particular blister(s) from which medicament powder is liberated. Thus, in this case, % ED is calculated as (ED/MD)×100%. It is desired that the % ED is at least 95% by weight, preferably more than 98% by weight.

Desirably the manifold herein also acts such as to increase the FP Fraction of the medicament powder that is made available at the chamber exit/mouthpiece for inhalation by the patient.

The term “fine particle fraction of emitted dose” or FP Fraction (ED) refers to the percentage of particles within a given Emitted Dose of aerosolized medicament that is of “respirable” size, as compared to the total emitted dose. A particle size range of from 1-6 μm is generally considered to be of “respirable” size. The FP Fraction (ED) may thus be calculated as a percentage of the Emitted Dose (ED). Thus, in this case, FP Fraction (ED) is calculated as (FPF/ED)×100%. It is desired that the FP Fraction (ED) is at least 25% by weight, preferably more than 30% by weight of the Emitted Dose of particles made available at the chamber exit/mouthpiece.

The FP Fraction may also be defined as a percentage of the measured dose (MD) contained within the particular blister(s) from which medicament powder is liberated. Thus, in this case, FP Fraction (MD) is calculated as (FPF/MD)×100%. It is desired that the FP Fraction (MD) is at least 25% by weight, preferably more than 30% by weight.

The manifold herein typically comprises a component part of a medicament dispenser device that is arranged to receive a blister pack having one or more blister pockets containing medicament in dry powder form.

In one aspect, the blister pack comprises multiple blisters for containment of medicament product in dry powder form. The blisters are typically arranged in regular fashion for ease of release of medicament therefrom. The blisters may have any suitable shape including those with a square, circular, ovular or rectangular profile.

Applicant has appreciated that the particular form including shape and cross-sectional area of the blister pocket affects the airflow properties, and particularly airflow resistance and pressure drop experienced at the open pocket when a patient inhales through the manifold herein.

By way of an example: a typical dose of medicament powder in a blister pocket is 17 μl. If the pocket took the form of a sphere, to accommodate this dose it would have a radius of 1.7 mm and a cross-sectional area of 8.0 $mm^2$ A flow of 60 l/min through an area of 8 $mm^2$ equates to an average velocity of 125 m/s. The pressure drop due to this flow will be approximately equal to:

$$\Delta P = \frac{K\rho v^2}{2}$$

(where ρ=density of air=1.3 $kg/m^3$, V=mean velocity=125 m/s and K=a geometric factor).

For a sudden contraction from a large cross-section to 8.0 $mm^2$, K=0.5 (approx.) so the pressure drop will be 5.1 kP. For a sudden expansion from 8.0 $mm^2$ to a large cross-sectional area K=1 (approx.) so the pressure drop will be 10.2 kPa Thus, a pocket geometry with a 8.0 $mm^2$ inlet and a 8.0 $mm^2$ outlet would have a resistance of 15.3 kPa at 60 liters/minute.

The resistivity of the pocket is =√(15.3)/60=0.065 (kPa) min/l so for a pressure drop of 2 kPa the flow would be =√(2)/0.065=221/min, this is about ⅓ of the total flow.

In the case of a blister pocket suitable for use with the well-known Diskus (trade mark) device as sold by GlaxoSmithKline Plc. And described in more, detail hereinbelow, the medicament powder is more stretched out (not in a sphere)

the cross-section in the pocket is in the region of 4 mm so the average velocity at 60 liters/minute would be 250 m/s.

For a simple inlet-outlet system (as above) the pressure drop at 60 liters/minute would be 61.2 kPa, the resistivity would be 0.130 $(kPa)^{0.5}$ minute/liter and the flow for a pressure drop of 2 kPa would be 11 liters/minute (18% of flow). For a blister pocket suitable for use with the well-known Diskus (trade mark) device, the resistivity would be about 0.15 $(kPa)^{0.5}$ minute/liter and the flow for a pressure drop of 2 kPa would be 9.4 liters/minute (16% of flow of 60 liters/minute).

In one aspect, the multi-dose blister pack comprises plural blisters arranged in generally circular fashion on a disc-form blister pack. An example of a medicament dispenser device suitable for dispensing medicament powder from such a disk-form blister pack is the well-known Diskhaler (trade mark) device as sold by GlaxoSmithKline Plc.

In another aspect, the blister pack is elongate in form, for example comprising a strip or a tape. Preferably, the blister pack is defined between two members peelably secured to one another. U.S. Pat. Nos. 5,860,419, 5,873,360 and 5,590,645 in the name of Glaxo Group Ltd describe medicament packs of this general type. In this aspect, the device is usually provided with an opening station comprising peeling means for peeling the members apart to access each medicament dose.

Suitably, the medicament dispenser device is adapted for use where the peelable members are elongate sheets that define a plurality of medicament containers spaced along the length thereof, the device being provided with indexing means for indexing each container in turn. More preferably, the medicament dispenser device is adapted for use where one of the sheets is a base sheet having a plurality of pockets therein, and the other of the sheets is a lid sheet, each pocket and the adjacent part of the lid sheet defining a respective one of the containers, the medicament dispenser device comprising driving means for pulling the lid sheet and base sheet apart at the opening station. An example of medicament dispenser device of this type is the well-known Diskus (trade mark) device as sold by GlaxoSmithKline Plc.

In one aspect, the blister form medicament pack comprises (a) a base sheet in which blisters are formed to define pockets therein containing a an inhalable dry powder medicament formulation;
(b) a lid sheet which is sealable to the base sheet except in the region of the blisters and mechanically peelable from the base sheet to enable release of said inhalable dry powder medicament formulation,
wherein said base sheet and/or said lid sheet have a laminate structure comprising (a) a first layer of aluminium foil; and (b) a second layer of polymeric material of thickness from 10 to 60 micron.

The base and lid sheets are typically sealed to one another over their whole width except for the forward end portions where they are typically not sealed to each other at all. Thus, separate base and lid sheet forward end portions are presented at the end of the strip.

Suitably, the polymeric material has a water vapour permeability of less than 0.6 g/(100 $inches^2$) (24 hours) (mil) at 25° C. The water vapour permeability is suitably measured by ASTM test method no. ASTM E96-635 (E).

Suitably, the polymeric material comprises a material selected from the group consisting of polypropylene (e.g. in oriented or cast form; standard or metallocene); polyethylene (e.g. in high, low or intermediate density form); polyvinyl chloride (PVC); polyvinylidene chloride (PVDC); polychlorotrifluoroethylene (PCTFE); cyclic olefin copolymer (COC); and cyclic olefin polymer (COP).

Suitably, the lid sheet comprises at least the following successive layers: (a) paper; bonded to (b) plastic film; bonded to (c) aluminium foil.

The aluminium foil typically coated with a layer (e.g. of heat seal lacquer; film or extrusion coating) for bonding to the base sheet material.

The thickness of each of the layers of the lid sheet may be selected according to the desired properties but is typically of the order of from 5 to 200 micron, particularly from 10 to 50 micron.

The plastic layer is in one aspect, suitably selected from polyester (non-oriented, monaxial, or biaxial oriented), polyamide, polypropylene or PVC. In another aspect the plastic film is an oriented plastic film, suitably selected from oriented polyamide (OPA); oriented polyester (OPET); and oriented polypropylene (OPP). The thickness of the plastic layer is typically from 5 to 40 μm, particularly 10 to 30 μm.

The thickness of the aluminium layer is typically from 10 to 60 μm, particularly 15 to 50 μm such as 20 to 30 μm.

In aspects, the paper layer comprises a paper/extrusion layer, optimally laminated to aluminium.

In one particular aspect, the lid sheet comprises at least the following successive layers: (a) paper; bonded to (b) polyester; bonded to (c) aluminium foil; that is coated with a heat seal lacquer for bonding to the base sheet. The thickness of each layer may be selected according to the desired properties but is typically of the order of from 5 to 200 micron, particularly from 10 to 50 micron.

The bonding may in aspects be provided as an adhesive bond (e.g. solvent-based adhesive wherein the solvent is organic or water-based); solvent free adhesive bond; extrusion laminated bond; or heat calandering.

Suitably, the base sheet comprises at least the following successive layers: (a) oriented polyamide (OPA); adhesively bonded to (b) aluminium foil; adhesively bonded to (c) a third layer of thickness from 10 to 60 micron comprising a polymeric material. The polymeric material preferably has a water vapour permeability of less than 0.6 g/(100 $inches^2$) (24 hours) (mil) at 25° C. The third layer will bond with the lid sheet, which is generally treated with a heat seal lacquer.

The thickness of each non-polymeric layer of the base sheet may be selected according to the desired properties but is typically of the order of from 5 to 200 micron, particularly from 20 to 60 micron. In accord with the invention, the thickness of the polymeric layer is selected to reduce moisture ingress, and is from 10 to 60 micron, particularly from 25 to 45 micron, preferably from 30 to 40 micron.

Suitably, the polymeric material is selected from the group consisting of polypropylene (in oriented or cast form; standard or metallocene); polyvinyl chloride (PVC); polyethylene (in high, low or intermediate density form); polyvinylidene chloride (PVDC); polychlorotrifluoroethylene (PCTFE); cyclic olefin copolymer (COC); and cyclic olefin polymer (COP). Optionally, other layers of material are also present.

Various known techniques can be employed to join the lid and base sheet and hence to seal the blisters. Such methods include adhesive bonding, radio frequency welding, ultrasonic welding and hot bar sealing.

The base sheet herein is particularly suitable for forming by 'cold form' methods, which are conducted at lower temperatures than conventional methods (e.g. at close to room temperature). Such 'cold form' methods are of particular utility where the medicament or medicament formulation for containment within the blister is heat sensitive (e.g. degrades or denatures on heating).

The blister pack is suitably receivable by a medicament dispenser comprising the manifold herein that also comprises a housing for receipt of the pack. In one aspect, the medicament dispenser has unitary form and the housing is integral therewith. In another aspect, the medicament dispenser is configured to receive a refill cassette and the housing forms part of that refill cassette.

Suitably, the interior of the housing is shaped, or alternatively provided with specific guiding features, to guide the blister form medicament pack appropriately into the housing. In particular, the guiding should ensure that the blister pack is suitably located to interact with internal mechanisms (e.g. indexing and opening mechanisms) of the housing.

Suitably, the medicament dispenser device has an internal mechanism for dispensing the distinct dry powder medicament doses carried by the blisters of the blister pack for administration to the patient (e.g. by inhalation). Suitably, the mechanism comprises, a) receiving means for receiving the blister pack;

b) release means for releasing a distinct medicament dose from a blister of the blister pack on receipt thereof by said receiving means;

c) a manifold herein, positioned to be in communication with the medicament dose releasable by said release means;

d) indexing means for individually indexing the distinct medicament doses of the blister pack.

The mechanism comprises receiving means (e.g. a receiving station) for receiving the blister pack.

The mechanism further comprises release means for releasing a distinct medicament dose from a blister of the blister pack on its receipt by the receiving station. The release means typically comprises means for mechanically peeling apart the blister strip.

A manifold herein is positioned to be in communication with the distinct medicament powder doses releasable by said release means. Delivery of the so-released medicament to the patient for inhalation thereby, is preferably through a single outlet that communicates with or forms an integral part with the manifold. The outlet may have any suitable form. In one aspect, it has the form of a mouthpiece for insertion into the mouth of a patient; and in another it has the form of a nozzle for insertion into the nasal cavity of a patient.

The mechanism also comprises indexing means for individually indexing the distinct medicament dose-containing blisters of the blister form medicament pack. Said indexing typically happens in sequential fashion, for example accessing dose portions sequentially arranged along the length of the blister form medicament pack.

Optionally, the medicament dispenser also includes counting means for counting each time a distinct medicament dose of the blister form medicament pack is indexed by said indexing means.

In one aspect, counting means is arranged to count each time a distinct medicament dose of the medicament carrier is indexed by said indexing means. Suitably, the indexing means and counting means engage directly or indirectly (e.g. via a coupling) with each other to enable counting of each indexation.

Suitably, the counting means is provided with (or communicates with) a display for displaying to the patient the number of distinct doses left to be taken or the number of doses taken.

In one preferred aspect, the medicament dispenser takes the form of a dispenser for use with a blister form medicament pack herein having multiple distinct pockets for containing inhalable medicament doses, wherein said pockets are spaced along the length of and defined between two peelable sheets secured to each other, said dispenser having an internal mechanism for dispensing the medicament doses contained within said medicament pack, said mechanism comprising, a) an opening station for receiving a pocket of the medicament pack;

b) peeling means positioned to engage a base sheet and a lid sheet of a pocket which has been received in said opening station for peeling apart such a base sheet and lid sheet, to open such a pocket, said peeling means including lid driving means for pulling apart a lid sheet and a base sheet of a pocket that has been received at said opening station;

c) a manifold herein, positioned to be in communication with an opened pocket through which medicament dose is deliverable from such an opened pocket;

d) indexing means for individually indexing the distinct pockets of the medicament pack.

Suitably, the indexing means comprises a rotatable index wheel having recesses therein, said index wheel being engageable with a medicament pack in use with said medicament dispenser such that said recesses each receive a respective pocket of the base sheet of a blister strip in use with said medicament dispenser.

According to another aspect of the present invention there is provided a medicament dispenser comprising (e.g. loaded with) at least one dry powder medicament-containing blister pack herein.

The manifold herein has hereinbefore been described in terms of its use with a medicament dispenser device suitable for dispensing medicament from the opened pocket of a blister pack. It will be appreciated that the manifold may also be employed for use with any medicament dispenser device suitable for dispensing medicament from an open cavity, wherein that cavity might for example, be provide by an opened capsule of a capsule form pack.

Thus, according to a further aspect of the invention there is provided a manifold for use in a medicament dispenser device for the delivery of medicament powder from an open cavity of a medicament pack, the manifold comprising a body, said body defining a chimney having a chimney inlet and a chimney exit for directing an airflow from said chimney inlet to said chimney exit;

the body further defining a chamber having a chamber inlet and a chamber exit, wherein the chimney exit and said chamber inlet lie side-by-side each other such that when said open cavity of said medicament pack is positioned adjacent thereto said airflow may be directed from the chimney exit to the chamber inlet via the open cavity to entrain said medicament powder and enable transport thereof in the airflow from the chamber inlet to said chamber outlet, and wherein the chimney is arranged to create turbulence in the airflow at the open cavity.

Suitably, the medicament dispenser herein is packaged within a package (i.e. an outer package, for example in the form of an overwrap) comprising a packaging material that is designed to reduce ingress of environmental moisture to the dispenser (and medicament pack thereof) packaged thereby.

The package is suitably formed any material which is impervious to or substantially impervious to moisture. The packaging material is preferably permeable to volatiles which may escape from the plastics forming the body of the inhaler and/or the blister form medicament pack, by diffusion or otherwise, thereby preventing a build-up in pressure.

BRIEF DESCRIPTION OF THE DRAWINGS

The invention will now be described with reference to the accompanying drawings in which:

FIGS. 16*a* and 16*b* show schematic sectional views of the early part of a further manifold herein.

DETAILED DESCRIPTION OF THE DRAWINGS

Figure 1:
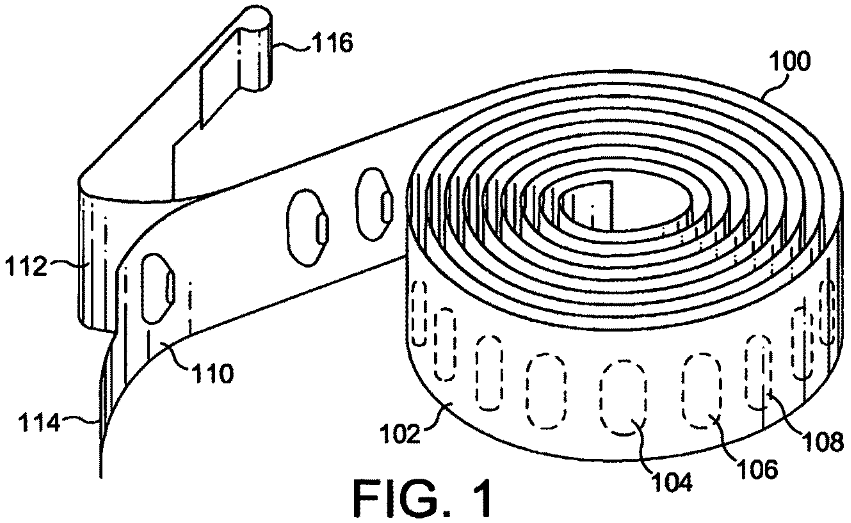
FIG. 1 shows a perspective view of the form of a medicament carrier of an elongate strip form suitable for use in accord with the present invention.

FIG. 1 shows a medicament carrier 100 that in elongate blister strip form for use in accord with the manifold for a medicament dispenser described herein. The medicament carrier comprises a flexible strip 102 defining a plurality of pockets 104, 106, 108 each of which would contain a portion of a dose of medicament which can be inhaled, in the form of powder.

The strip comprises a base sheet 110 in which blisters are formed to define the pockets 104, 106, 108 and a lid sheet 112 which is hermetically sealed to the base sheet except in the region of the blisters in such a manner that the lid sheet 112 and the base sheet 110 can be peeled apart. The sheets 110, 112 are sealed to one another over their whole width except for the leading end portions 114, 116 where they are preferably not sealed to one another at all. The lid 112 and base 110 sheets are formed of a laminate and are preferably adhered to one another by heat sealing.

The strip 102 is shown as having elongate pockets 104, 104, and 108 that run transversely with respect to the length of the strip 102. This is convenient in that it enables a large number of pockets 104, 106, 108 to be provided in a given strip 102 length. The strip 102 may, for example, be provided with sixty or one hundred pockets but it will be understood that the strip 102 may have any suitable number of pockets.

Figure 2:
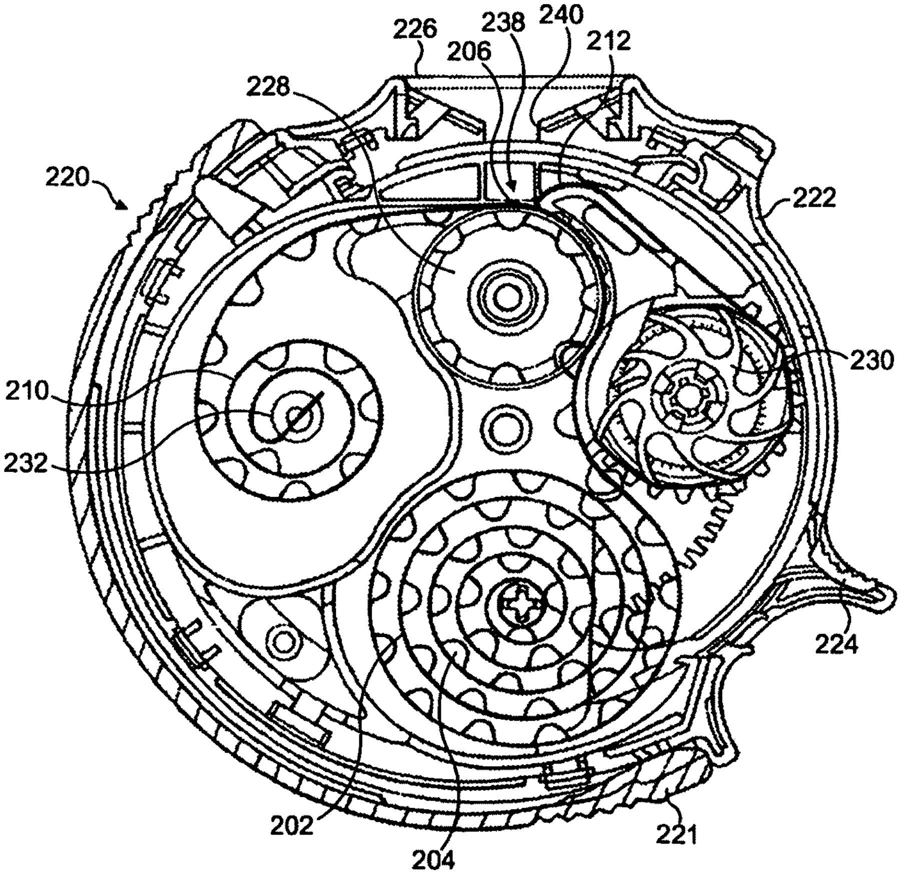
FIG. 2 shows a sectional plan view of a medicament dispenser device comprising a medicament carrier and suitable for use in accord with the present invention.

FIG. 2 shows a medicament dispenser in the form of a dry powder inhaler that may be adapted to comprise the manifold described herein. The inhaler 220 is of the general type sold by GlaxoSmithKline Plc under the trade mark Diskus®.

In more detail, the inhaler 220 is arranged to dispense unit doses of medicament powder from pockets 204 of a medicament carrier in the form of an elongate blister strip 202. The inhaler is comprised of an outer casing 221 enclosing medicament strip 202 within body 222. The elongate blister strip 202 suitably has the form shown in FIG. 1. The patient uses the inhaler by holding the device 220 to his mouth, depressing lever 224, and inhaling through mouthpiece 226. Depression of lever 224 activates the internal mechanism of the inhaler, such that the lid 212 and base 210 sheets of coiled medicament blister strip 202 are separated by peeling apart at index wheel 228 as a resulting of the pulling action of lid sheet take-up wheel 230. It will be appreciated that once peeled apart, the lid sheet 212 is coiled around the take-up wheel 230. In turn, the separated base sheet 210 coils around base sheet take-up wheel 232. A unit dose of powdered medicament within opened blister pocket 206 is released at opening station 238 and may be inhaled by the patient through manifold 240 and ultimately mouthpiece 226. The exact form of the manifold 240 is not visible in FIG. 2, but will have a form in accord with the present invention and as shown in later Figures herein.

Figure 3A:
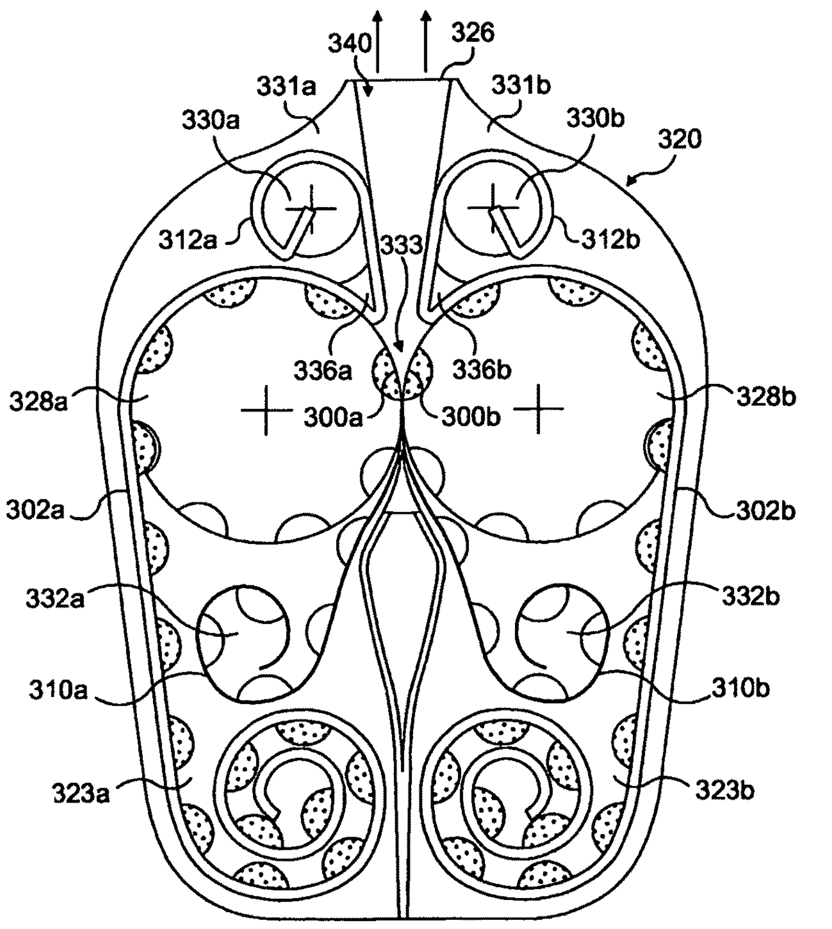
FIG. 3*a* shows a sectional plan view of a second medicament dispenser device comprising a medicament carrier and suitable for use in accord with the present invention.

FIG. 3*a* illustrates the base unit 320 of a medicament dispenser for use in accord with the manifold herein. In use, a cover (not shown) would be provided to the base unit 320. First and second medicament-containing blister strips 302*a*, 302*b* are positioned within respective left and right chambers 323*a*, 323*b* of the base unit 320. Each blister strip 302*a*, 302*b* engages a respective multi-pocket index wheel 328*a*, 328*b*, and successive pockets are thereby guided towards a commonly located opening station 338. The rotation of the index wheels 328*a*, 328*b* is coupled. At the opening station 338, the lid foil 312*a*, 312*b* and base foil 310*a*, 310*b* parts of each strip 302*a*, 302*b* are peelably separable about a beak 336*a*, 336*b*. The resulting empty base foil 310*a*, 310*b* coils up in respective base take-up chambers 332*a*, 332*b*. The used lid foil 312*a*, 312*b* is fed over its respective beak 336*a*, 336*b* and coiled about a lid take-up spindle 330*a*, 330*b* in the lid take-up chamber 331*a*, 331*b*.

Released powder form medicament from opened pockets 306*a*, 306*b* of both the first 302*a* and second 302*b* strips is accessible via manifold 340 to the mouthpiece 326 for inhalation by the patient. The manifold 340 defines a particular geometry through which the released powders travel for mixing thereof prior to delivery at the mouthpiece 326. The exact form of the manifold 340 is not visible in FIG. 3, but will have a form in accord with the present invention and as shown in later Figures herein. The dispenser of FIG. 3 enables different medicament types to be stored separately in each of the strips 302*a*, 302*b* but the release and delivery thereof to the patient as a 'mixed' multi-active combined inhaled product.

Figure 3B:
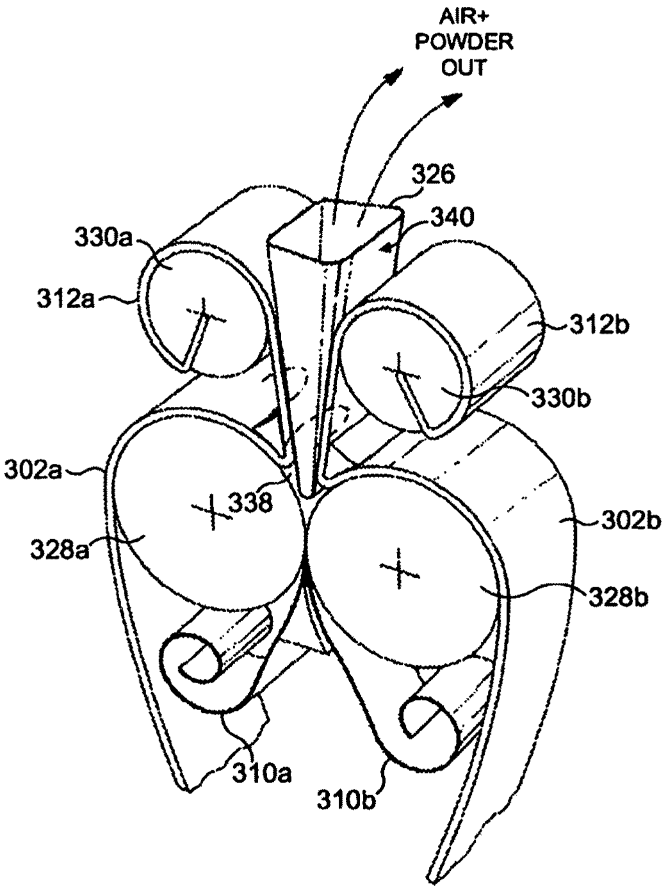
FIG. 3*b* shows a perspective view of a detail of the medicament dispenser device of FIG. 3*a;*

FIG. 3*b* shows the release of medicament from the open pockets in more detail. The patient breathes in through the mouthpiece 326 resulting in negative pressure being transmitted through manifold 340 to the opened pockets (not visible) of the strips 302*a*, 302*b* at the opening station 338. This typically results in the creation of a venturi effect which results in the powder contained within each of the opened pockets 302*a*, 302*b* being drawn out through the common manifold 340 and thence to the mouthpiece 326 for inhalation by the patient.

Figure 4:
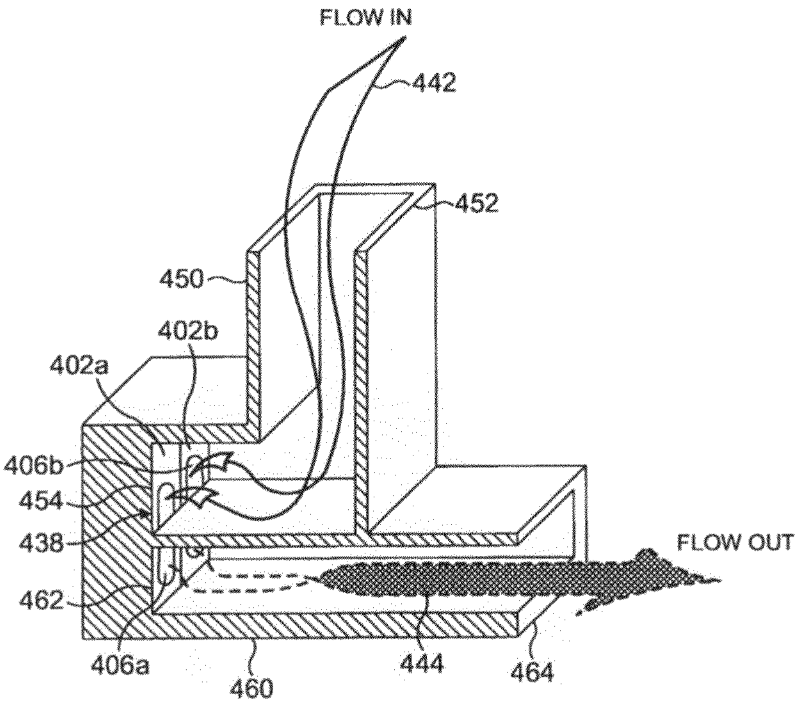
FIG. 4 shows a sectional side view of a prior art manifold in accord with the present invention.

FIG. 4 illustrates a prior art manifold design suitable for use in a variation of a medicament dispenser device of the type shown in FIGS. 3*a* and 3*b*.

First and second medicament components of the combination medicament product for delivery are contained within open blister pockets 406*a*, 406*b* of two elongate blister strips 402*a*, 402*b*. At common opening station 438, the opened pockets 406*a*, 406*b* are exposed to an inward airflow 442 (created in response to the inward breath of a patient), which flows through chimney 450 from chimney inlet 452 to chimney exit 454, which lies adjacent the opened pockets 406*a*, 406*b*. The airflow is then channeled through the opened pockets 406*a*, 406*b* to entrain the powdered medicament products contained respectively therein and thence to transport the entrained powder product 364 through chamber 460 from chamber inlet 462 to chamber outlet 464 for patient inhalation thereof. It will be appreciated that the airflow 442 to the opened blister pockets 406*a*, 406*b* is essentially laminar and non-turbulent.

Figure 5A:
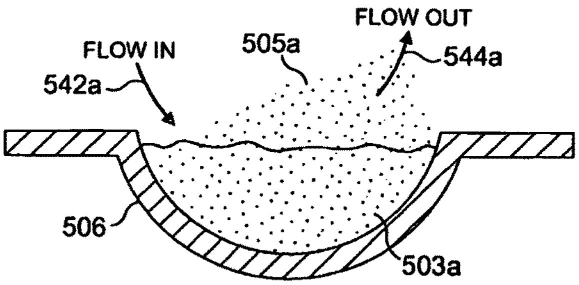
FIGS. 5*a* and 5*b* show sectional side views of prior art mechanisms for entraining medicament powder from an open blister pocket.
Figure 5B:
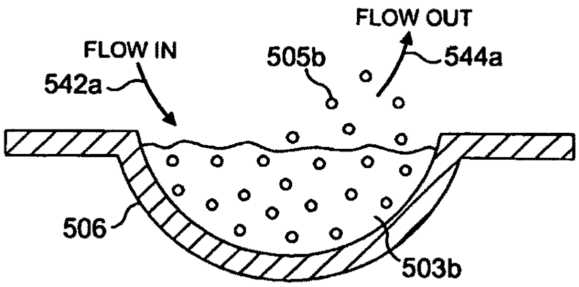

FIGS. 5*a* and 5*b* show prior art examples of illustrative powder entrainment mechanisms at an opened blister pocket 506.

In FIG. 5*a*, an essentially laminar and non-turbulent airflow 542*a* is directed towards an open blister pocket 506 containing a bulk of medicament powder 503*a* having essentially non-cohesive character. The mechanism for powder entrainment may be seen to be a ‘saltation’ process in which small, discrete medicament particles 505*a* are lifted from the surface of the bulk powder 503*a* and carried off in the exit airflow 544*a*.

In FIG. 5*b*, an essentially laminar and non-turbulent airflow 542*a* is directed towards an open blister pocket 506 containing a bulk of medicament powder 503*b* having essentially cohesive character (e.g. a sticky or agglomerated product). The mechanism for powder entrainment may be seen to be a process in which chunks of associated (e.g. aggregated or agglomerated) medicament particles 505*b* lift away from the surface of the bulk powder 503*b* and carried off in the exit airflow 544*a*.

Figure 5C:
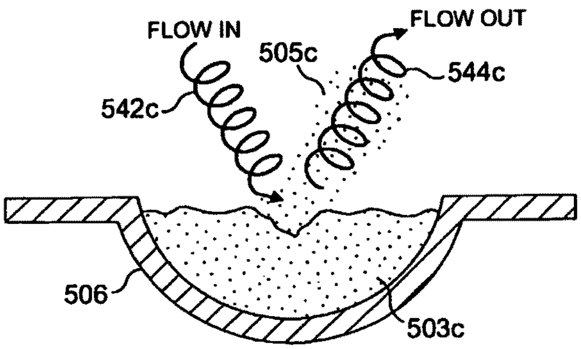
FIGS. 5*c* and 5*d* show sectional side views of mechanisms for entraining medicament powder from an open blister pocket herein.
Figure 5D:
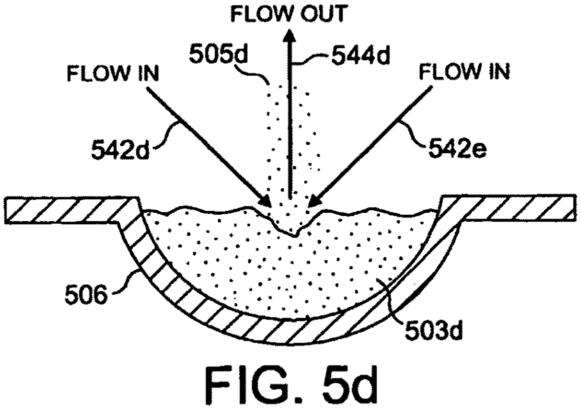

FIGS. 5*c* and 5*d* show examples of illustrative powder entrainment mechanisms at an opened blister pocket 506 in accord with the present invention.

In FIG. 5*c*, a turbulent vortex-like airflow 542*c* is directed towards an open blister pocket 506 containing a bulk of medicament powder 503*c* having essentially non-cohesive character. The mechanism for powder entrainment may be seen to be a disruptive process in which small, discrete medicament particles 505*c* are lifted in response to turbulence/high shear stress from the surface of the bulk powder 503*c* and carried off in the exit airflow 544*c*.

In FIG. 5*d*, plural, laminar airflows 542*d*, 542*e* are directed at different and conflicting angles towards an open blister pocket 506 containing a bulk of medicament powder 503*d* having essentially non-cohesive character. The mechanism for powder entrainment may be seen to be a disruptive process in which small, discrete medicament particles 505*d* are lifted in response to the resulting turbulence/high shear stress from the surface of the bulk powder 503*d* and carded off in the exit airflow 544*d*.

Figure 6A:
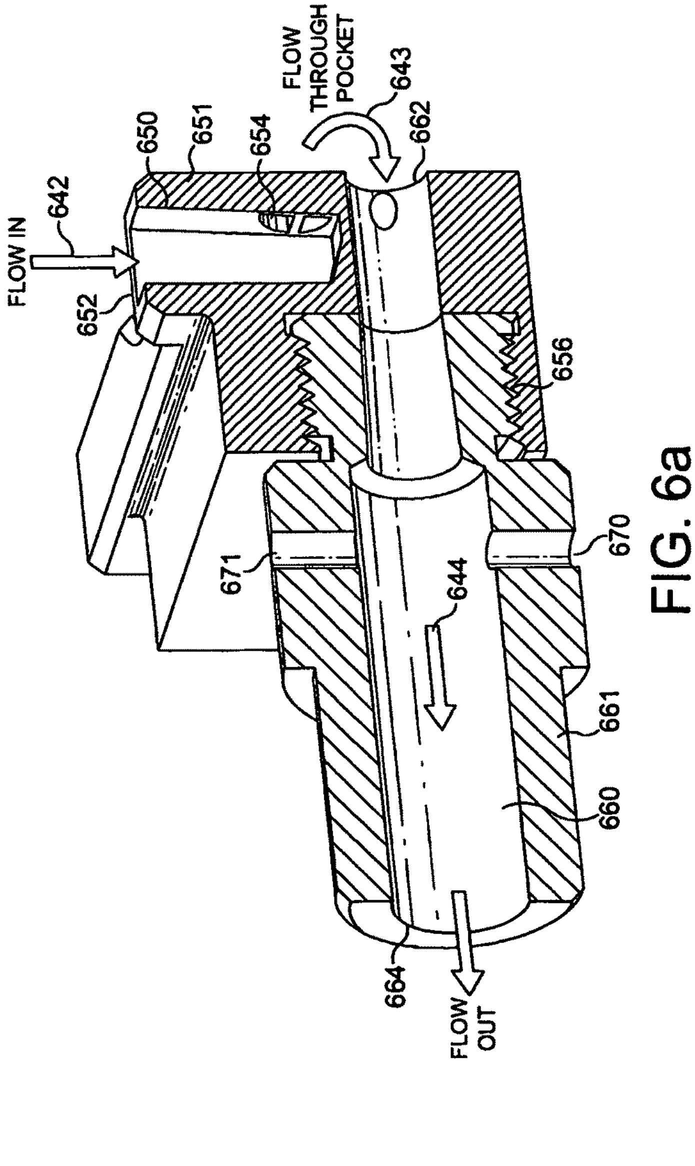
FIG. 6*a* shows a sectional view in perspective of a manifold herein.

FIG. 6*a* illustrates a manifold design herein suitable for use in a medicament dispenser device for the delivery of medicament powder from an open blister pocket of a blister pack. The manifold of FIG. 6*a* is particularly suitable for use in a variation of a medicament dispenser device of the type shown in FIG. 2.

Referring now to FIG. 6*a*, the manifold may be seen to comprise a first manifold body part 651 defining a chimney 650 having a chimney inlet 652 and a chimney exit 654. In use, the chimney 650 directs an inward airflow 642 from the chimney inlet 652 to the chimney exit 654. A second mid-manifold body part 661 (shown separately in FIG. 6*b*) is threadedly received at screw-fixing point 656. [In general terms screw-fixing is not preferred, and it may be appreciated that two manifold parts 651, 661 may alternatively be provided as a single moulding]. In combination, the manifold body parts 651, 661 define a chamber 660 having a chamber inlet 662 and a chamber exit 664. The chamber 660 has a diameter of 7 mm. It will noted that the diameter of the chamber 660 is narrower at the end closest to the chamber inlet 662 and broadest at the end closes to the chamber exit 664 and that the slope 666 marks the transition from the narrow to broad diameter.

It will be seen that the chimney exit 654 and chamber inlet 662 holes are positioned to be adjacent to each other such that when an open blister pocket (not shown) lies adjacent thereto the airflow 643 is directed via the open pocket from the chimney exit 654 to the chamber inlet 662 as shown. This airflow 643 at the open blister pocket entrains the powder contents of the pocket and enables the transport thereof in the airflow 644 from the chamber inlet 662 to the chamber outlet 664, and thence to the inhaling patient.

The chamber 660 is provided with two bleed holes 670, 671 located diametrically opposite to each other. It will be appreciated that in use, the bleed holes 670, 671 act such as to direct bleed jets into the chamber 660. It will also be appreciated that because of the opposing orientation of the bleed holes 670, 671 such bleed jets will interact with each other to create regions of high shear.

Figure 8:
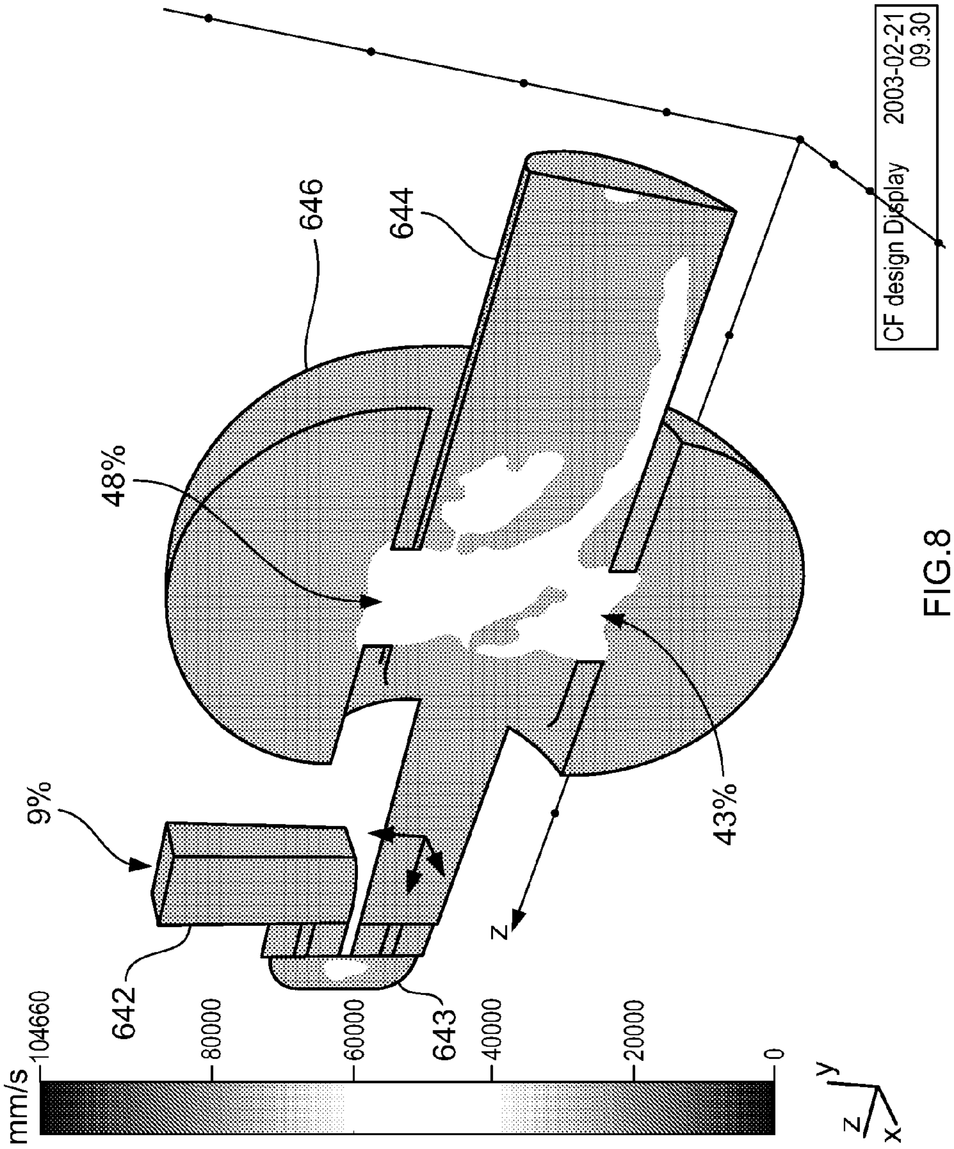
FIG. 8 shows a plot of the airflow profile on inhalation through the manifold of FIG. 6*a;*

Characteristics of the resultant airflow may be better understood by reference to FIG. 8, which shows a plot of the velocity profile of the airflow when a patient breathes through the chamber inlet 664. It may be seen that only 9% of the total airflow is that part of the airflow 642, 643 that is drawn through the chimney 650 and open pocket. Respectively, 43% and 48% of the airflow is drawn through each of the bleed holes 670, 671. The bleed jets interact at high shear region 646, which ‘cuts across’ the airflow 644 through the chamber 660 (of diameter 7 mm) that in use, transports the entrained particles. The bleed jets also interact with the walls of the chamber 660 to create further regions of high shear. The effect of the entrained particles experiencing the regions of high shear 646 is to cause break-up of the powder particles, thereby resulting in an improvement of the FP fraction for the particles delivered to the inhaling patient.

Figure 6B:
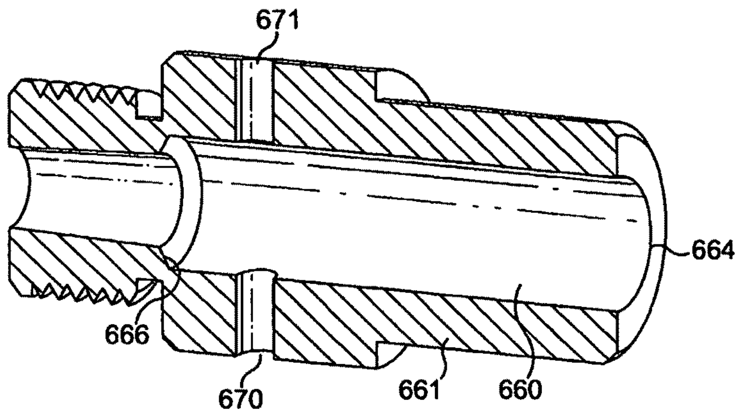
FIG. 6*b* shows a sectional view in perspective of the mid-manifold part of the manifold of FIG. 6*a;*
Figure 7:
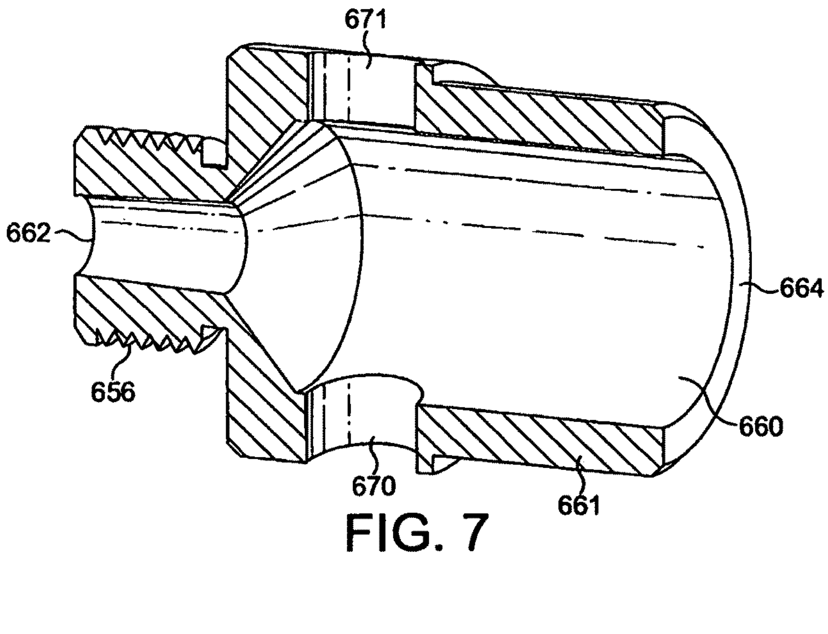
FIG. 7 shows a sectional view in perspective of an alternative mid-manifold part for use with the manifold of FIG. 6*a;*

FIG. 7 shows a variation of the second mid-manifold body part of FIG. 6*b*, which can also be used in combination with the first manifold body part 651 of FIG. 6*a*. It will be seen that the diameter of the chamber 660 of FIG. 7 is significantly greater than that of FIG. 6*a*, but all other features thereof are similar. The chamber 660 of FIG. 7 has a diameter of 14 mm.

Figure 9:
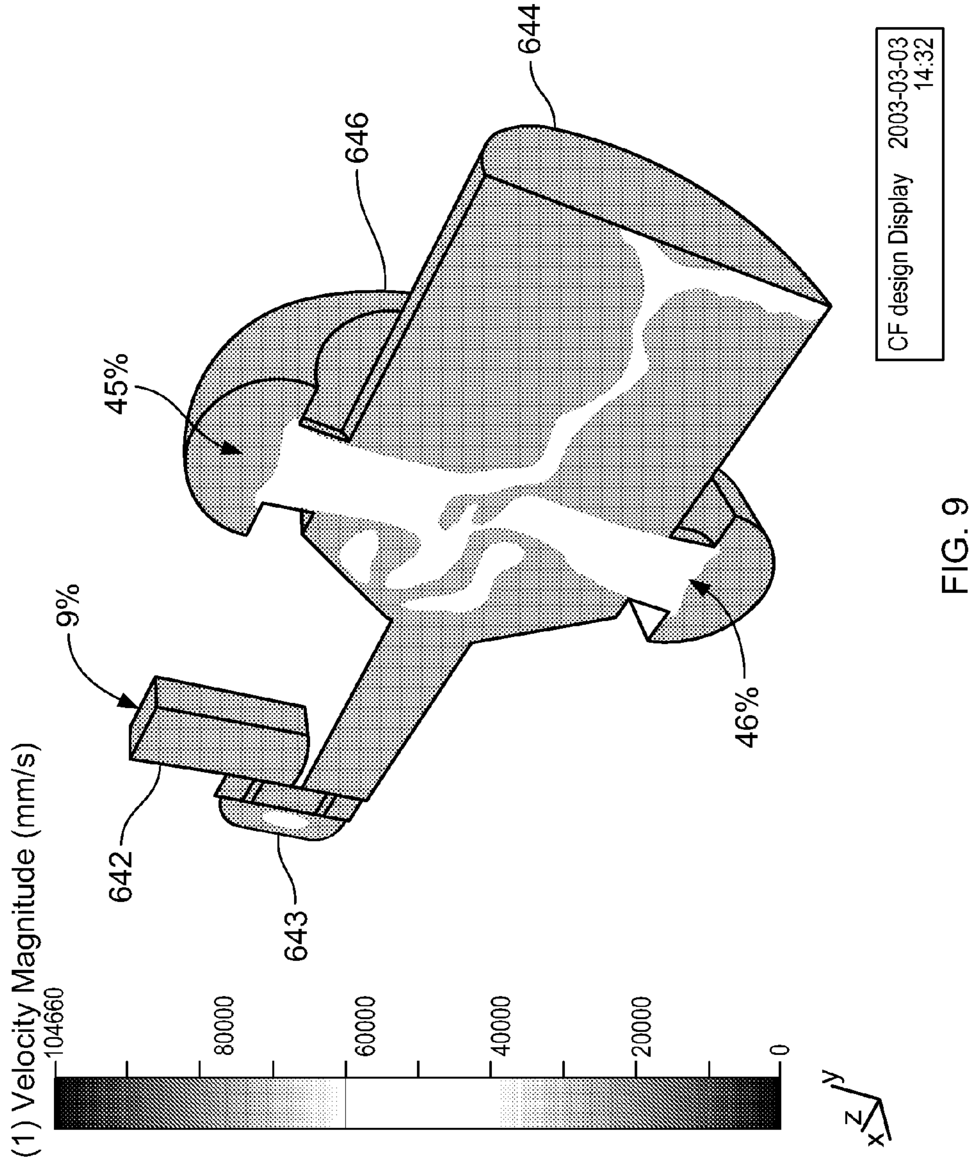
FIG. 9 shows a plot of the airflow profile on inhalation through the manifold of FIG. 6*a* when used with the alternative mid-manifold part of FIG. 7.

Characteristics of the resultant airflow obtained using the variation of FIG. 7 together with the first manifold part 650 of FIG. 6*a* may be better understood by reference to FIG. 9, which shows a plot of the velocity profile of the airflow when a patient breathes through the chamber inlet 664. Similarly to the plot of FIG. 9, only a small proportion (9%) of the total airflow is that part of the airflow 642, 643 that is drawn through the chimney 650 and open pocket. Respectively, 46% and 45% of the airflow is drawn through each of the bleed holes 670, 671. The bleed jets interact at high shear region 646, which 'cuts across' the airflow 644 through the chamber 660 (of diameter 14 mm) that carries the entrained particles. The scale and disruptive (i.e. powder break-up) effect of the high shear region is however, less than that obtained with the smaller diameter chamber 660 of the mid-manifold part of FIGS. 6*a* and 6*b* because the bleed jets do not interact with the walls of the chamber 660 of FIG. 7 to create regions of high shear thereat.

Figure 10:
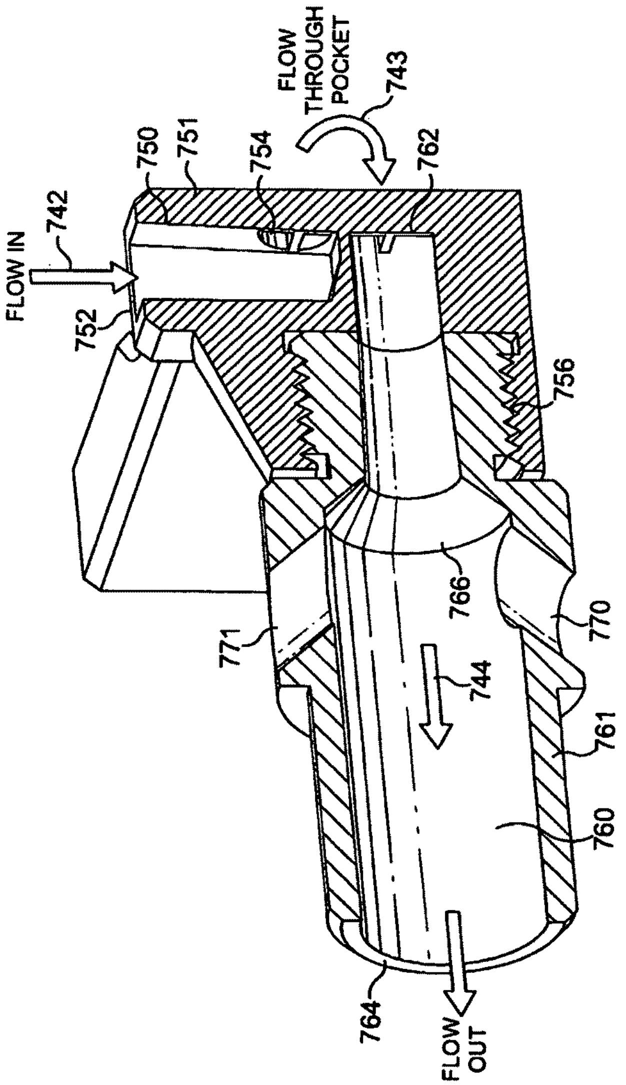
FIG. 10 shows a sectional view in perspective of another manifold herein.

FIG. 10 illustrates a manifold design herein that is a variation of the manifold of FIG. 6*a*.

The manifold of FIG. 10 may be seen to comprise a first manifold body part 751 defining a chimney 750 having a chimney inlet 752 and a chimney exit 754. In use, the chimney 750 directs an inward airflow 742 from said chimney inlet 752 to said chimney exit 754. A second mid-manifold body part 761 is threadedly received at screw-fixing point 756. [In general terms screw-fixing is not preferred, and it may be appreciated that two manifold parts 751, 761 may alternatively be provided as a single moulding]. In combination, the manifold body parts 751, 761 define a chamber 760 having a chamber inlet 762 and a chamber exit 764. It will noted that the diameter of the chamber 760 is narrower at the end closest to the chamber inlet 762 and broadest at the end closes to the chamber exit 764 and that the slope 766 marks the transition from the narrow to broad diameter.

It will be seen that the chimney exit 754 and chamber inlet 762 holes are positioned to be adjacent to each other such that when an open blister pocket lies adjacent thereto the airflow 743 is directed via the open pocket (not shown) from the chimney exit 754 to the chamber inlet 762 as shown. This airflow 743 at the open blister pocket entrains the powder contents of the pocket and enables the transport thereof in the airflow 744 from the chamber inlet 762 to the chamber outlet 764, and thence to the inhaling patient.

The chamber 760 is provided with two bleed channels 770, 771 located diametrically opposite to each other and angled relative to each other. It will be appreciated that in use, the bleed holes 770, 771 act such as to direct bleed jets into the chamber 760, and that because of the orientation of the bleed holes 770, 771 such bleed jets will interact with each other to create high shear region 746, which 'cuts across' the airflow 744 through the chamber 760 that carries the entrained particles. The effect of the entrained particles experiencing this region of high shear 746 will be to cause break-up of the powder particles, thereby resulting in an improvement of the FP fraction for the particles delivered to the inhaling patient.

Figure 11:
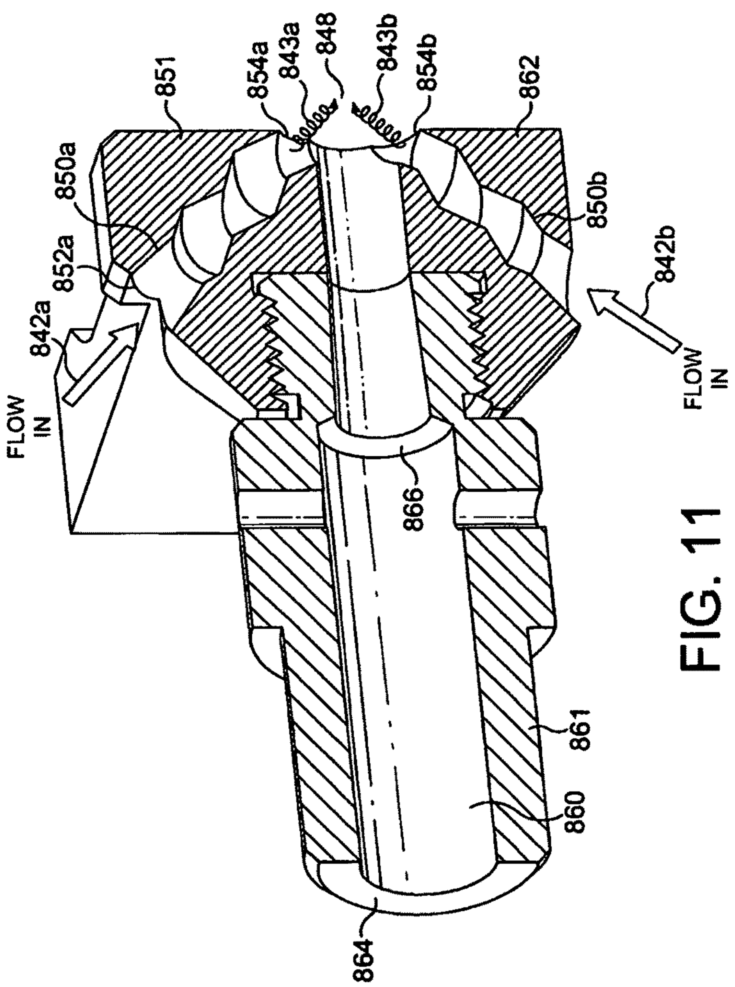
FIG. 11 shows a sectional view in perspective of a further manifold herein.

FIG. 11 illustrates a manifold design herein that is a further variation of the manifold of FIG. 6*a*.

The manifold of FIG. 11 may be seen to comprise a first manifold body part 851 defining a first and second chimney 850*a*, 850*b* each of which has a chimney inlet 852*a*, 852*b* and a chimney exit 854*a*, 854*b*. In use, each chimney 850*a*, 850*b* directs an inward airflow 842*a*, 842*b* from its chimney inlet 852*a*, 852*b* to its chimney exit 854*a*, 854*b*. It will be noted that each chimney 850*a*, 850*b* has a generally helical inner form and that the chimneys 850*a*, 850*b* locate at an angle relative to each other. The airflow 843*a*, 843*b* that emerges from the respective chimney exits 854*a*, 854*b* thus, also has a helical character and interacts at high shear point 848, which also corresponds in use, to the position of the open pocket (not shown).

The resultant airflow 843*a*, 843*b* at the open pocket thus, corresponds essentially to that shown in previous FIG. 5*d*, in which a region of disruptive high shear 848 is created at the open pocket to assist in aerosolization of the powder contained therein.

The second mid-manifold body part 761 of the manifold of FIG. 11 corresponds exactly to that of FIGS. 6*a* and 6*b* and is not therefore described further.

The manifold herein may be arranged such as to delay the emptying of the medicament powder from the blister pocket. FIGS. 12*a* to 16*b* illustrate different means of achieving such delay.

Figure 12A:
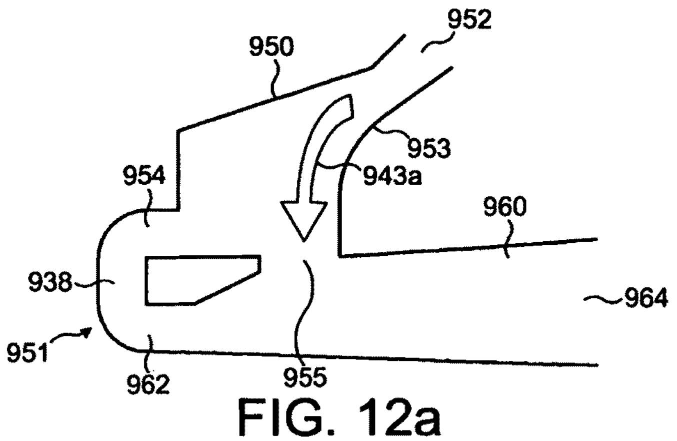
FIGS. 12*a* and 12*b* show schematic sectional views of the early part of a manifold herein.
Figure 12B:
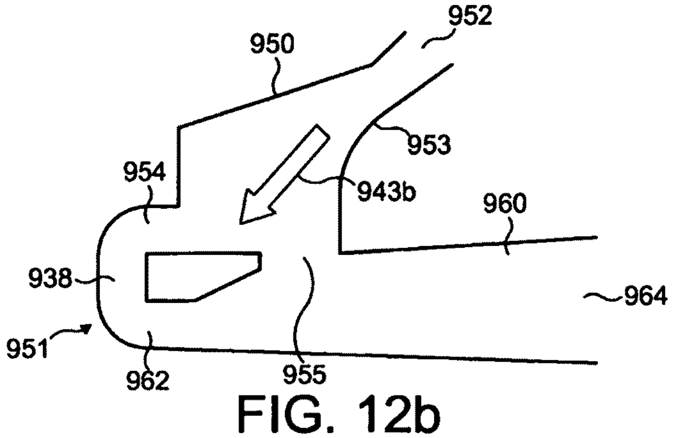

Referring now to FIGS. 12*a* and 12*b*, there is shown an early part of a manifold body 951 that defines a chimney 950 having a chimney inlet 952, a first chimney exit 954 and a second chimney exit 955. It will seen that first chimney exit 954 is directed towards pocket emptying station 938, which in use, accommodates an open blister pocket (not shown). It will further be seen that second chimney exit 955 is directed towards manifold chamber 960. It may be appreciated that any airflow that proceeds through the second chimney exit 955 'by-passes' the pocket opening station 938 and open pocket received thereby, and instead proceeds straight into the manifold chamber 960. The chamber 960 itself has a chamber inlet 962 (leading from the pocket opening station 938) and a chamber exit 964.

FIGS. 12*a* and 12*b* show different aspects of use of the manifold 951. In FIG. 12*a*, light airflow 943*a* (e.g. provided by the start of the inward breath of an inhaling patient) is drawn through the chimney 950 and tends to 'cling' to the inner surface 953 of the chimney such that it is directed towards the second chimney exit 955 and directly into the chamber 960, thereby by-passing the pocket opening station 938. As a result, none of the powder contents of an open blister pocket at the opening station 938 will be transported to the chamber 960. Without wishing to be bound by theory, it is believed that the 'clinging' behaviour of the light airflow 943*a* in this mode of operation is as a result of the Couanda effect.

In FIG. 12*b*, stronger airflow 943*b* (e.g. provided by the mid and full-strength part of the inward breath of an inhaling patient) is drawn through the chimney 950 and does not 'cling' to the inner surface 953 of the chimney. The airflow 943*b* is directed towards the first chimney exit 954 and hence to the pocket opening station 938. As a result, the powder contents of an open blister pocket at the opening station 938 are aerosolised and then transported (entrained in the airflow) to the chamber 960 via chimney inlet 962. The entrained particles are subsequently delivered to the patient for inhaled delivery at the chimney exit 964.

Overall, it will be noted that particle entrainment occurs only when a stronger airflow 943*b* is provided. Thus, a delay is provided to emptying of the contents of the open pocket whilst a sufficiently strong airflow 943*b* is building up.

Figure 13:
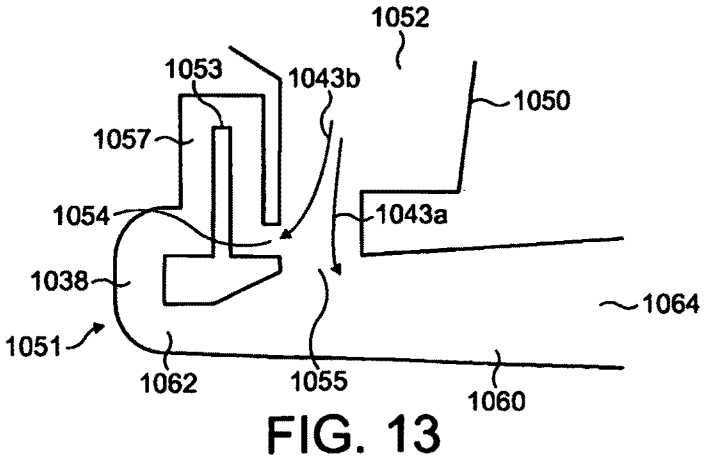
FIG. 13 shows a schematic sectional view of the early part of another manifold herein.

Referring now to FIG. 13, there is shown an early part of a manifold body 1051 that defines a chimney 1050 having a chimney inlet 1052, a first chimney exit 1054 and a second chimney exit 1055. It will seen that first chimney exit 1054 is directed towards pocket emptying station 1038, which in use, accommodates an open blister pocket (not shown). The flow path from chimney exit 1054 to pocket opening station comprises labyrinthine channel 1057 defined by the manifold body 1051 and guide piece 1058. It will further be seen that second chimney exit 1055 is directed towards manifold chamber 1060. It may be appreciated that any airflow that proceeds through the second chimney exit 1055 'by-passes' the pocket opening station 1038 and open pocket received thereby, and instead proceeds straight into the manifold chamber 1060. The chamber 1060 itself has a chamber inlet 1062 (leading from the pocket opening station 1038) and a chamber exit 1064.

Overall, the path length from first chimney exit 1054 through labyrinthine channel 1057 to opening station 1038 and thence, to chamber 1060 via chamber inlet 1062 is significantly greater than that of the path from second chimney exit 1055 direct into the chamber 1060. Thus, overall a delay is set up between air flowing into the chamber 1060 (via the second chimney exit) and the transport of entrained powder from an open pocket at the opening station 1038 to the chamber 1060.

Figure 14A:
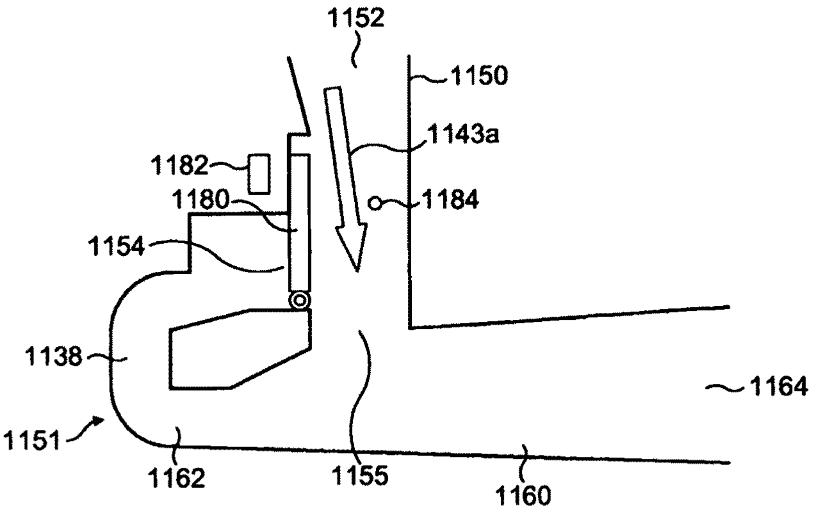
FIGS. 14*a* and 14*b* show schematic sectional views of the early part of a further manifold herein.
Figure 14B:
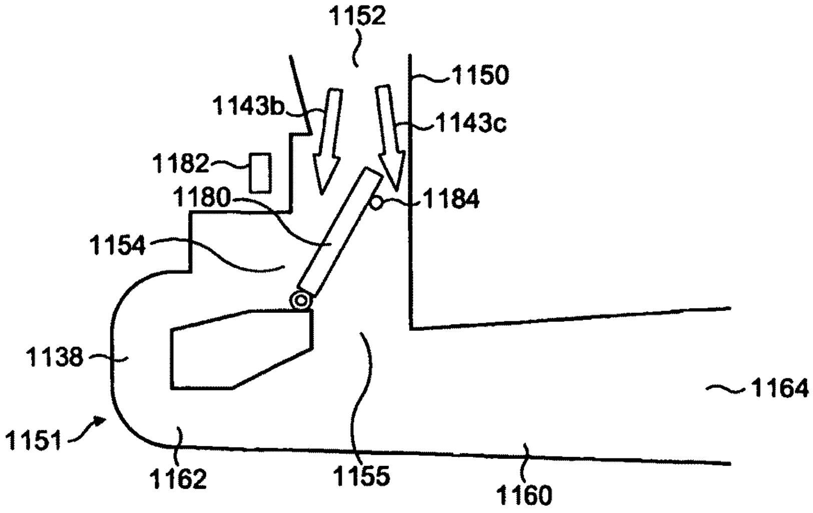

Referring now to FIGS. 14*a* and 14*b*, there is shown an early part of a manifold body 1151 that defines a chimney 1150 having a chimney inlet 1152, a first chimney exit 1154 and a second 'by pass' chimney exit 1155. It will seen that first chimney exit 1154 is directed towards pocket emptying station 1138, which in use, accommodates an open blister pocket (not shown). It will further be seen that second 'by-pass' chimney exit 1155 is directed towards manifold chamber 1160. It may be appreciated that any airflow that proceeds through the second chimney exit 1155 'by-passes' the pocket opening station 1138 and open pocket received thereby, and instead proceeds straight into the manifold chamber 1160. The chamber 1160 itself has a chamber inlet 1162 (leading from the pocket opening station 1138) and a chamber exit 1164.

The first chimney exit 1154 is provided with a closure in the form of a pivotally mounted metal flap 1180 that interacts with light magnetic catch 1182. The flap 1180 is pivotally movable from a first position (as shown in FIG. 14*a*) in which the first chimney exit 1154 is closed off to a second position (as shown in FIG. 14*b*) when the first chimney exit 1154 is open and the flap 1180 rests against stop 1184. The purpose of the stop 1184 is to ensure that when in the second position the flap 1180 does not entirely obscure the second 'by pass' chimney exit 1155. In an alternative embodiment, the stop 1184 is not present, and therefore in the second position the flap 1180 fully closes off the second 'by pass' chimney exit 1155.

FIGS. 14*a* and 14*b* show different aspects of use of the manifold 1151. In FIG. 14*a*, light airflow 1143*a* (e.g. provided by the start of the inward breath of an inhaling patient) is drawn through the chimney 1150 and is directed towards the second chimney exit 1155 and directly into the chamber 1160, thereby by-passing the pocket opening station 1138. As a result, none of the powder contents of an open blister pocket at the opening station 1138 will be transported to the chamber 1160.

In FIG. 14*b*, stronger airflow 1143*b*, 1143*c* (e.g. provided by the mid and full-strength part of the inward breath of an inhaling patient) is also drawn through the chimney 1150. As a result of this, negative pressure gradually builds up at the surface of the flap 1180, which eventually becomes sufficient to detach the stop 1180 from its magnetic catch, thereby opening up the first chimney exit 1154. Part of the airflow 1143*b* is thus, directed via the opened-up first chimney exit 1154 and hence to the pocket opening station 1138. As a result, the powder contents of an open blister pocket at the opening station 1138 are aerosolised and then transported (entrained in the airflow) to the chamber 1160 via chimney inlet 1162. The entrained particles are subsequently delivered to the patient for inhaled delivery at the chimney exit 1164. In tandem, a second part of the airflow 1143*c* flows via second chimney exit 1155 directly into the chamber 1160.

Overall, it will be noted that particle entrainment occurs only when a sufficiently strong airflow 1143*b*, 1143*c* is provided to move the flap 1180 and open up the first chimney exit 1154. Thus, a delay is provided to emptying of the contents of the open pocket whilst a sufficiently strong airflow 1143*b*, 1143*b* is building up.

Figure 15A:
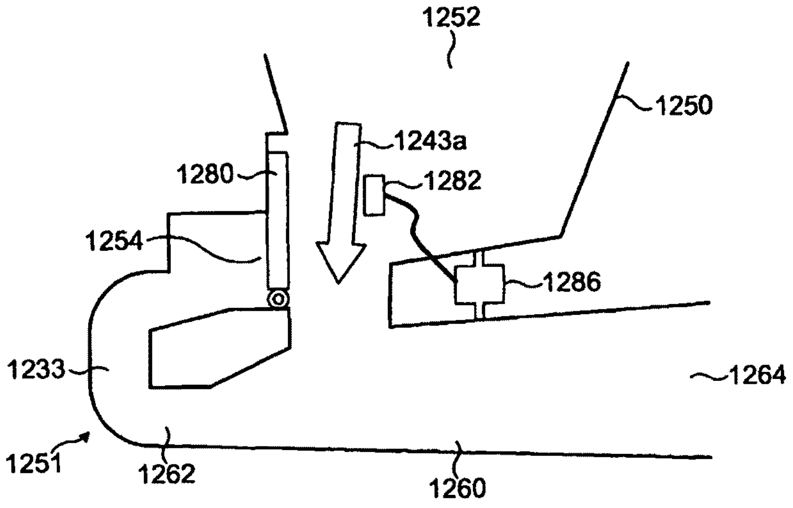
FIGS. 15*a* and 15*b* show schematic sectional views of the early part of a further manifold herein.
Figure 15B:
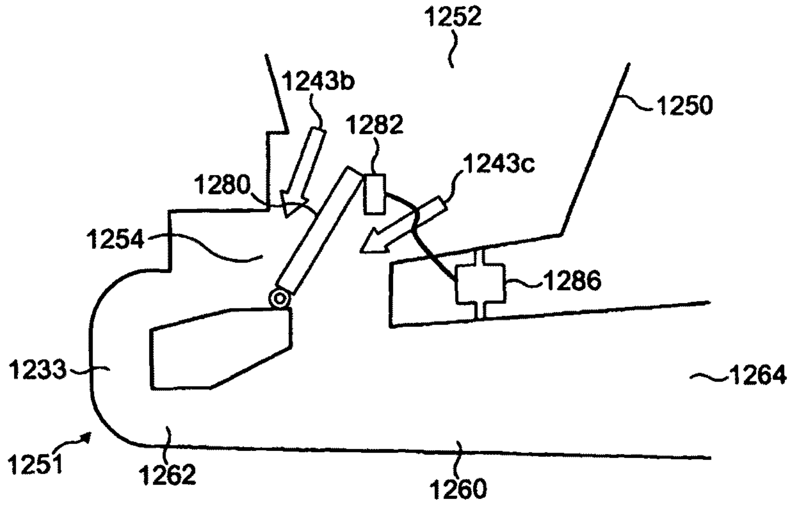

Referring now to FIGS. 15*a* and 15*b*, there is shown an early part of a manifold body 1251 that is a variation of that shown in FIGS. 14*a* and 14*b*.

The manifold body 1251 defines a chimney 1250 having a chimney inlet 1252, a first chimney exit 1254 and a second 'by pass' chimney exit 1255. It will seen that first chimney exit 1254 is directed towards pocket emptying station 1238, which in use, accommodates an open blister pocket (not shown). It will further be seen that second 'by-pass' chimney exit 1255 is directed towards manifold chamber 1260. It may be appreciated that any airflow that proceeds through the second chimney exit 1255 'by-passes' the pocket opening station 1238 and open pocket received thereby, and instead proceeds straight into the manifold chamber 1260. The chamber 1260 itself has a chamber inlet 1262 (leading from the pocket opening station 1238) and a chamber exit 1264.

The first chimney exit 1254 is provided with a closure in the form of a pivotally mounted metal flap 1280 that is set up to interact with electromagnet 1282. The flap 1280 is pivotally movable from a first position (as shown in FIG. 15*a*) to which it is preferentially biased and, in which the first chimney exit 1254 is closed off to a second position (as shown in FIG. 15*b*) when the first chimney exit 1254 is open and the flap 1280 rests against electromagnet 1282 that also acts as a stop. The purpose of the stop is to ensure that when in the second position the flap 1280 does not entirely obscure the second 'by pass' chimney exit 1255. In an alternative embodiment, the stop 1282 is not present, and therefore in the second position the flap 1280 fully closes off the second 'by pass' chimney exit 1255.

The electromagnet 1282 is responsive to differential pressure transformer 1286 that is set up to monitor air pressure in the chimney 1250. Once a certain threshold air pressure is exceeded the differential pressure transducer 1286 sends a signal to activate the electromagnet 1282, thereby attracting flap 1280 to it.

FIGS. 15*a* and 15*b* show different aspects of use of the manifold 1251. In FIG. 15*a*, light airflow 1243*a* (e.g. provided by the start of the inward breath of an inhaling patient) is drawn through the chimney 1250. The differential pressure transducer 1286 only detects air pressure below the threshold level and the electromagnet 1282 is de-activated such that the flap 1280 remains in the first position. All of the airflow 1243*a* is therefore directed towards the second chimney exit 1255 and directly into the chamber 1260, thereby bypassing the pocket opening station 1238. As a result, none of the powder contents of an open blister pocket at the opening station 1238 will be transported to the chamber 1260.

In FIG. 14*b*, stronger airflow 1243*b*, 1243*c* (e.g. provided by the mid and full-strength part of the inward breath of an inhaling patient) is also drawn through the chimney 1250. As a result of this, the differential pressure transducer 1286 detects air pressure above the threshold level and the electromagnet 1282 is activated such that the flap 1280 moves to the second position, thereby opening up the first chimney exit 1254. Part of the airflow 1243*b* is thus, directed via the opened-up first chimney exit 1254 and hence to the pocket opening station 1238. As a result, the powder contents of an open blister pocket at the opening station 1238 are aerosolised and then transported (entrained in the airflow) to the chamber 1260 via chimney inlet 1262. The entrained particles are subsequently delivered to the patient for inhaled delivery at the chimney exit 1264. In tandem, a second part of the airflow 1243*c* flows via second chimney exit 1255 directly into the chamber 1260.

Overall, it will be noted that particle entrainment occurs only when a sufficiently strong airflow 1243*b*, 1243*c* is provided to exceed the threshold air pressure detected by the differential pressure transducer 1286*b* and result in activation of the electromagnet 1282 to move the flap 1280 and open up the first chimney exit 1254. Thus, a delay is provided to emptying of the contents of the open pocket whilst a sufficiently strong airflow 1243*b*, 1243*b* is building up.

Figure 16A:
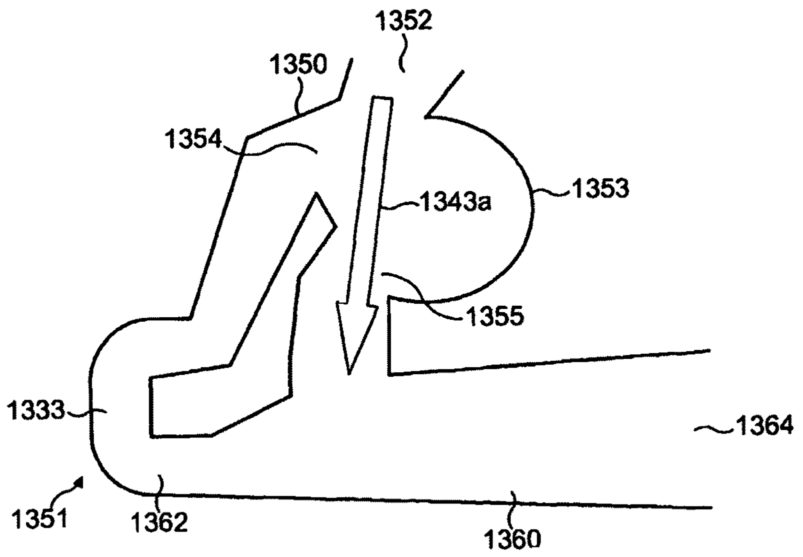
Figure 16A:
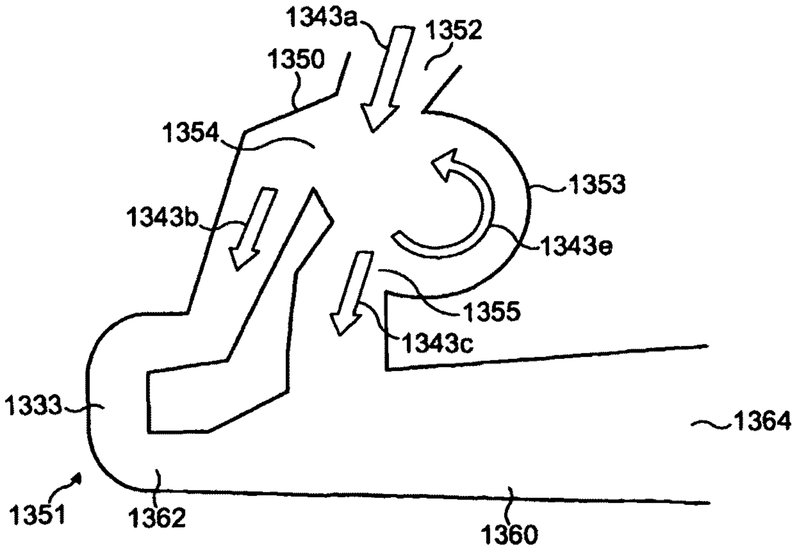

Referring now to FIGS. 16*a* and 16*b*, there is shown an early part of a manifold body 1351 that defines a chimney 1350 having a chimney inlet 1352, a first chimney exit 1354 and a second chimney exit 1355. The chimney is also provided with swirl chamber 1353, the purpose of which will become clearer from the later description. It will seen that first chimney exit 1354 is directed towards pocket emptying station 1338, which in use, accommodates an open blister pocket (not shown). It will further be seen that second chimney exit 1355 is directed towards manifold chamber 1360. It may be appreciated that any airflow that proceeds through the second chimney exit 1355 'by-passes' the pocket opening station 1338 and open pocket received thereby, and instead proceeds straight into the manifold chamber 1360. The chamber 1360 itself has a chamber inlet 1362 (leading from the pocket opening station 1338) and a chamber exit 1364.

FIGS. 16*a* and 16*b* show different aspects of use of the manifold 1351. In FIG. 16*a*, light airflow 1343*a* (e.g. provided by the start of the inward breath of an inhaling patient) is drawn through the chimney 1350 such that it is directed straight towards the second chimney exit 1355 and directly into the chamber 1360, thereby by-passing the pocket opening station 1338. As a result, none of the powder contents of an open blister pocket at the opening station 1338 will be transported to the chamber 1360.

In FIG. 16*b*, stronger airflow 1343*d* (e.g. provided by the mid and full-strength part of the inward breath of an inhaling patient) is drawn through the chimney 1350 and part of this stronger flow is drawn into the swirl chamber 1353 as shown where it forms a re-circulation jet 1343*e* that impacts upon and separates the main airflow 1343*d* into separate and distinct flows 1343*b*, 1343*c*. The first part of the separated airflow 1343*b* is directed towards the first chimney exit 1354 and hence to the pocket opening station 1338. As a result, the powder contents of an open blister pocket at the opening station 1338 are aerosolised and then transported (entrained in the airflow) to the chamber 1360 via chimney inlet 1362. The entrained particles are subsequently delivered to the patient for inhaled delivery at the chimney exit 1364. The second part of the separated airflow 1343*c* flows via second chimney exit 1355 directly into the chamber 1360.

Overall, it will be noted that particle entrainment occurs only when a stronger airflow 1343*d* is provided such that a recirculation jet 1343*e* forms in the swirl chamber 1353. Thus, a delay is provided to emptying of the contents of the open pocket whilst a sufficiently strong airflow 1343*d* is building up.

Figure 17:
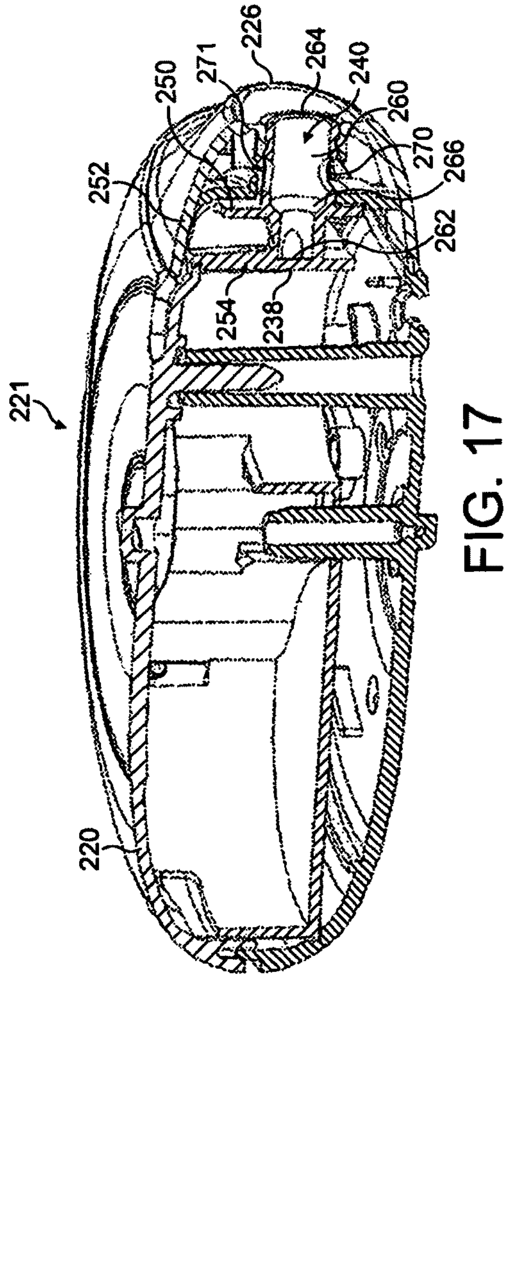
FIG. 17 shows a sectional view of a medicament dispenser device incorporating a manifold herein.

FIG. 17 shows in cut-away view part of the casing 221 of the medicament dispenser of FIG. 2 adapted to incorporate a manifold herein (e.g. as shown in FIG. 6*a*).

In more detail, the outer casing 221 is designed to enclose a medicament strip (not shown) within body 222. In use, a unit dose of powdered medicament contained within an opened blister pocket is presented at opening station 238 and may be inhaled by the patient through manifold 240 and ultimately mouthpiece 226. The manifold 240 may be seen to comprise chimney 250 having a chimney inlet 252 and a chimney exit 254. In use, the chimney 250 directs inward airflow from the chimney inlet 252 to the chimney exit 254. The manifold 240 also defines a chamber 260 having a chamber inlet 262 and a chamber exit 264. The diameter of the chamber 260 is narrower at the end closest to the chamber inlet 262 and broadest at the end closes to the chamber exit 264 and slope 266 marks the transition from the narrow to broad diameter.

The chimney exit 254 and chamber inlet 262 holes are positioned to be adjacent to each other such that when an open blister pocket (not shown) lies adjacent thereto at the opening station 238 the inward airflow is directed via the open pocket from the chimney exit 254 to the chamber inlet 262. This airflow at the open blister pocket entrains the powder contents of the pocket and enables the transport thereof in the airflow from the chamber inlet 262 to the chamber outlet 264, and thence to the inhaling patient.

The chamber 260 is provided with two bleed holes 270, 271 located diametrically opposite to each other. In use, the bleed holes 270, 271 act such as to direct bleed jets into the chamber 260 and because of the opposing orientation of the bleed holes 270, 271 such bleed jets interact with each other to create regions of high shear.

It may be appreciated that any of the parts of the device or any component thereof which contacts medicament may be coated with materials such as fluoropolymer materials (e.g. PTFE or FEP) that reduce the tendency of medicament to adhere thereto. Any movable parts may also have coatings applied thereto which enhance their desired movement characteristics. Frictional coatings may therefore be applied to enhance frictional contact and lubricants (e.g. silicone oil) used to reduce frictional contact as necessary.

The manifold herein is suitable for use in a medicament dispenser device for dispensing powdered medicament formulations, particularly for the treatment of respiratory disorders such as asthma and chronic obstructive pulmonary disease (COPD), bronchitis and chest infections.

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); anti-infectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α, 9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); $\alpha_4$ integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy) acetyl]amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

The formulated medicament product may in aspects, be a mono-therapy (i.e. single active medicament containing) product or it may be a combination therapy (i.e. plural active medicaments containing) product.

Suitable medicaments or medicament components of a combination therapy product are typically selected from the group consisting of anti-inflammatory agents (for example a corticosteroid or an NSAID), anticholinergic agents (for example, an $M_1$, $M_2$, $M_1/M_2$ or $M_3$ receptor antagonist), other β2-adrenoreceptor agonists, antiinfective agents (e.g. an antibiotic or an antiviral), and antihistamines. All suitable combinations are envisaged.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17β-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g. chemokine antagonists) or inhibitors of cytokine synthesis. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Suitable phosphodiesterase 4 (PDE4) inhibitors include compounds that are known to inhibit the PDE4 enzyme or which are discovered to act as a PDE4 inhibitor, and which are only PDE4 inhibitors, not compounds which inhibit other members of the PDE family as well as PDE4. Generally it is preferred to use a PDE4 inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4.

A method for determining $IC_{50}$s ratios is set out in U.S. Pat. No. 5,998,428 which is incorporated herein in full by reference as though set out herein. See also PCT application WO 00/51599 for an another description of said assay.

Suitable PDE4 inhibitors include those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity.

A further refinement of this standard is that of one wherein the PDE4 inhibitor has an $IC_{50}$ ratio of about 0.1 or greater; said ratio is the ratio of the $IC_{50}$ value for competing with the binding of 1 nM of $[^3H]$R-rolipram to a form of PDE4 which binds rolipram with a high affinity over the $IC_{50}$ value for inhibiting the PDE4 catalytic activity of a form which binds rolipram with a low affinity using 1 μM$[^3H]$-cAMP as the substrate.

Most suitable are those PDE4 inhibitors which have an $IC_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl) cyclohexan-1-one and cis-[4-cyano-4-(3-cyclopropylmethoxy-4-difluoromethoxyphenyl) cyclohexan-1-ol]; these are examples of compounds which bind preferentially to the low affinity binding site and which have an $IC_{50}$ ratio of 0.1 or greater.

Other suitable medicament compounds include: cis-4-cyano-4-[3-(cyclopentyloxy)-4-methoxyphenyl]cyclohexane-1-carboxylic acid (also known as cilomalast) disclosed in U.S. Pat. No. 5,552,438 and its salts, esters, pro-drugs or physical forms; AWD-12-281 from elbion (Hofgen, N. et al. 15th EFMC Int Symp Med Chem (Sep. 6-10, Edinburgh) 1998, Abst P. 98; CAS reference No. 247584020-9); a 9-benzyladenine derivative nominated NCS-613 (INSERM); D4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (Sep. 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10 bS*)-9-ethoxy-1,2,3,4,4a,10b-hexahydro-8-methoxy-2-methylbenzo[c][1,6] naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T440 (Tanabe Seiyaku; Fuji, K. et al. J Pharmacol Exp Ther, 1998, 284(1): 162), and T2585.

Suitable anticholinergic agents are those compounds that act as antagonists at the muscarinic receptor, in particular those compounds, which are antagonists of the $M_1$ and $M_2$ receptors. Exemplary compounds include the alkaloids of the belladonna plants as illustrated by the likes of atropine, scopolamine, homatropine, hyoscyamine; these compounds are normally administered as a salt, being tertiary amines.

Particularly suitable anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-5346-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-354), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. Examples include ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chiropheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a PDE4 inhibitor.

Particularly suitable anti-histamines include methapyrilene and loratadine.

In respect of combination products, co-formulation compatibility is generally determined on an experimental basis by known methods and may depend on chosen type of medicament dispenser action.

The medicament components of a combination product are suitably selected from the group consisting of anti-inflammatory agents (for example a corticosteroid or an NSAID), anticholinergic agents (for example, an $M_1$, $M_2$, $M_1/M_2$ or $M_3$ receptor antagonist), other $\beta_2$-adrenoreceptor agonists, anti-infective agents (e.g. an antibiotic or an antiviral), and antihistamines. All suitable combinations are envisaged.

Suitably, the co-formulation compatible components comprise a $\beta_2$-adrenoreceptor agonist and a corticosteroid; and the co-formulation incompatible component comprises a PDE4 inhibitor, an anti-cholinergic or a mixture thereof. The $\beta_2$-adrenoreceptor agonists may for example be salbutamol (e.g., as the free base or the sulphate salt) or salmeterol (e.g., as the xinafoate salt) or formoterol (eg as the fumarate salt). The corticosteroid may for example, be a beclomethasone ester (e.g., the dipropionate) or a fluticasone ester (e.g., the propionate) or budesonide.

In one example, the co-formulation compatible components comprise fluticasone propionate and salmeterol, or a salt thereof (particularly the xinafoate salt) and the co-formulation incompatible component comprises a PDE4 inhibitor, an anti-cholinergic (e.g. ipratropium bromide or tiotropium bromide) or a mixture thereof.

In another example, the co-formulation compatible components comprise budesonide and formoterol (e.g. as the fumarate salt) and the co-formulation incompatible component comprises a PDE4 inhibitor, an anti-cholinergic (e.g. ipratropium bromide or tiotropium bromide) or a mixture thereof.

Generally, powdered medicament particles suitable for delivery to the bronchial or alveolar region of the lung have an aerodynamic diameter of less than 10 micrometers, preferably from 1-6 micrometers. Other sized particles may be used if delivery to other portions of the respiratory tract is desired, such as the nasal cavity, mouth or throat. The medicament may be delivered as pure drug, but more appropriately, it is preferred that medicaments are delivered together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient.

Particles of powdered medicament and/or excipient may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

The excipient may be included with the medicament via well-known methods, such as by admixing, co-precipitating and the like. Blends of excipients and drugs are typically formulated to allow the precise metering and dispersion of the blend into doses. A standard blend, for example, contains 13000 micrograms lactose mixed with 50 micrograms drug, yielding an excipient to drug ratio of 260:1. Dosage blends with excipient to drug ratios of from 100:1 to 1:1 may be used. At very low ratios of excipient to drug, however, the drug dose reproducibility may become more variable.

The medicament dispenser device described herein is in one aspect suitable for dispensing medicament for the treatment of respiratory disorders such as disorders of the lungs and bronchial tracts including asthma and chronic obstructive pulmonary disorder (COPD). In another aspect, the invention is suitable for dispensing medicament for the treatment of a condition requiring treatment by the systemic circulation of medicament, for example migraine, diabetes, pain relief e.g. inhaled morphine.

Accordingly, there is provided the use of the medicament dispenser device herein for the treatment of a respiratory disorder, such as asthma and COPD. Alternatively, the present invention provides a method of treating a respiratory disorder such as, for example, asthma and COPD, which comprises administration by inhalation of an effective amount of medicament product as herein described from a medicament dispenser device herein.

The amount of any particular medicament compound or a pharmaceutically acceptable salt, solvate or physiologically functional derivative thereof which is required to achieve a therapeutic effect will, of course, vary with the particular compound, the route of administration, the subject under treatment, and the particular disorder or disease being treated. The medicaments for treatment of respiratory disorders herein may for example, be administered by inhalation at a dose of from 0.0005 mg to 10 mg, preferably 0.005 mg to 0.5 mg. The dose range for adult humans is generally from 0.0005 mg to 100 mg per day and preferably 0.01 mg to 1 mg per day.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. A manifold for use in a medicament dispenser device for the delivery of medicament powder from an open blister pocket of a blister pack, the manifold comprising a body, said body defining a chimney having a chimney inlet and a chimney exit for directing an airflow from said chimney inlet to said chimney exit;

the body further defining a chamber having a chamber inlet and a chamber exit, wherein the chimney exit and said chamber inlet lie side-by-side each other such that when said open blister pocket of said blister pack is positioned adjacent thereto said airflow may be directed from the chimney exit to the chamber inlet via the open blister pocket to entrain said medicament powder and enable transport thereof in the airflow from the chamber inlet to said chamber outlet, and wherein the chimney is arranged to create turbulence in the airflow at the open blister pocket, wherein the manifold comprises plural chimney exits, located at an angle relative to each other of from 150° to 30° such that in use, plural airflow jets are directed at different and conflicting angles towards the open blister pocket; and wherein an obstacle is positioned within the chimney to create a non-linear airflow.

2. A manifold according to claim 1, wherein the obstacle is a divider.

3. A manifold according to claim 2, wherein said divider defines a knife-edge profile.

* * * * *

UNITED STATES PATENT AND TRADEMARK OFFICE

CERTIFICATE OF CORRECTION

PATENT NO. : 8,590,531 B2
APPLICATION NO. : 11/722185
DATED : November 26, 2013
INVENTOR(S) : Collin John Rouse et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1900 days.

Signed and Sealed this
Eighth Day of July, 2014

Michelle K. Lee
*Deputy Director of the United States Patent and Trademark Office*